(12) United States Patent
Krishnan

(10) Patent No.: US 8,163,312 B2
(45) Date of Patent: Apr. 24, 2012

(54) HERBAL FORMULATION FOR PREVENTION AND TREATMENT OF DIABETES AND ASSOCIATED COMPLICATIONS

(75) Inventor: G. Geetha Krishnan, Patparganj (IN)

(73) Assignee: Innoveda Biological Solutions (P) Ltd., New Delhi (IN)

( * ) Notice: Subject to any disclaimer, the term of this patent is extended or adjusted under 35 U.S.C. 154(b) by 0 days.

(21) Appl. No.: 13/063,804

(22) PCT Filed: Sep. 17, 2009

(86) PCT No.: PCT/IN2009/000510
§ 371 (c)(1),
(2), (4) Date: May 31, 2011

(87) PCT Pub. No.: WO2010/032267
PCT Pub. Date: Mar. 25, 2010

(65) Prior Publication Data
US 2011/0236488 A1    Sep. 29, 2011

(30) Foreign Application Priority Data

| Sep. 22, 2008 | (IN) | 2221/DEL/2008 |
| Jun. 15, 2009 | (IN) | 1221/DEL/2009 |
| Jun. 15, 2009 | (IN) | 1222/DEL/2009 |
| Jun. 15, 2009 | (IN) | 1223/DEL/2009 |
| Jun. 15, 2009 | (IN) | 1224/DEL/2009 |

(51) Int. Cl.
*A61K 36/00* (2006.01)
*A61K 36/9066* (2006.01)
*A61K 36/8905* (2006.01)
*A61K 9/14* (2006.01)
*A61K 36/906* (2006.01)

(52) U.S. Cl. ............ 424/725; 424/489; 424/756

(58) Field of Classification Search ............ None
See application file for complete search history.

(56) References Cited

U.S. PATENT DOCUMENTS

| 4,826,684 | A  | 5/1989 | Hakky |
| 4,908,207 | A  | 3/1990 | Hakky |
| 6,551,627 | B1 | 4/2003 | Yoon et al. |
| 2004/0116394 | A1 | 6/2004 | Mukherjee et al. |
| 2008/0206372 | A1 | 8/2008 | Agreda Navajas et al. |

FOREIGN PATENT DOCUMENTS

| CA | 2532332 | 2/2005 |
| GB | 190505856 | 10/1905 |
| JP | 10127256 | 5/1998 |
| JP | 2000080044 | 3/2000 |
| JP | 2005320281 | 11/2005 |
| JP | 2006008528 | 1/2006 |
| JP | 2006056836 | 3/2006 |
| JP | 2006104094 | 4/2006 |
| JP | 2006232781 | 9/2006 |
| KR | 20020011015 | 2/2002 |
| WO | 2006030426 | 3/2006 |

OTHER PUBLICATIONS

International Preliminary Report on Patentability for PCT/IN2009/000510 mailed Mar. 22, 2011, 8 pages.

*Primary Examiner* — Qiuwen Mi
(74) *Attorney, Agent, or Firm* — Meyertons, Hood, Kivlin, Kowert & Goetzel, P.C.; Eric B. Meyertons

(57) ABSTRACT

An herbal formulation for prevention and treatment of Diabetes and associated complications comprising extracts from selected Indian medicinal herbs. The invention has associate formulations for different diabetes related complications, which are individually useful in clinical requirements such as improving renal health and preventing renal diseases, preventing diabetic retinopathy and prevention and treatment for oxidative damage to heart and blood vessels. The invention is versatile and can be processed into extracts/concentrates and further pharmacologically modified to tablets or capsules or granules or syrups or herbal health drink or inhalable herbal medicinal preparations or ocular preparations or transdermal absorbable preparations such as ointments/gels or injectable medicine.

12 Claims, No Drawings

HERBAL FORMULATION FOR PREVENTION AND TREATMENT OF DIABETES AND ASSOCIATED COMPLICATIONS

FIELD OF THE INVENTION

The present invention relates to an herbal formulation for the prevention and treatment of diabetes and the associated complications. The present invention particularly relates to an herbal formulation useful for controlling/reducing the blood glucose level significantly and for the prevention/management/treatment of diabetes related complications. The formulation of the present invention not only efficiently controls the Type 2 diabetes but also offers reversal possibilities in pre-diabetes and thereby a possible preventive option for Type 2 diabetes mellitus and the associated complications.

The present invention also relates to a herbal formulation for the prevention and treatment of diabetes mellitus.

The present invention also relates to a herbal formulation for prevention and treatment of renal complications associated with diabetes consequently reducing the serum creatinine levels, which is elevated due to reasons which can be attributed to the kidneys and their functional and structural integrity.

The present invention also relates to a herbal formulation for the prevention and treatment of retinopathy associated with diabetes. The formulation of the present invention not only efficiently controls the progress of diabetic retinopathy but also offers reversal possibilities in such cases.

The present invention also relates to a herbal formulation for prevention and treatment of oxidative damage to heart and its blood vessels associated with diabetes useful for reducing oxidative damage caused to the cardiac musculature and blood vessel walls, and treating hypertension.

Diabetes Mellitus is the most prevalent metabolic disorder among humans with enormous implications on social health and financial wealth. This is characterized by poor regulation of blood glucose levels in human beings. Other than blood glucose levels the long term effects of the disease involves all major systems and organs of the body including the Heart and blood vessels, Kidneys, Liver, Eyes and the nervine systems. The improper nutrition of the cells due to lack of insulin, leads to structural and functional irregularities in the cells, including the waste they generate and its management. Diabetes mellitus also predisposes cardiac failure and renal failure.

Presently, this disorder is managed by taking drugs falling into the following categories:

i) pancreatic stimulators:—This class of drugs helps to stimulate the pancreas, leading to increased secretion of insulin. This addresses the diabetes caused by inadequate insulin secretion.

ii) Insulin sensitizers:—This category of drugs improves the cell's sensitivity to the presence of insulin, thereby improving the uptake of glucose into the cells, leading to better blood sugar control.

iii) Insulin:—This is exogenously supplemented in the case of people suffering from both type I and type II diabetes.

Diabetes is a lifestyle disease and cannot be cured. The current therapies mentioned above are therefore only a blood sugar management mechanism. As diabetes is a chronic, long-duration disease, these drugs need to be taken on a sustained basis. Currently, available synthetic drugs suffer from concomitant side effects caused due to long duration of usage. Literature survey indicates that cardiovascular mortality was higher in patients with oral hypoglycemics than in those treated with diet and exercise alone or with insulin.

Sulphonylureas cause hypoglycemia as a side effect. Biguanides cause lactic acidosis. Oral hypoglycemia-drugs also cause GIT irritation, weight gain, hypertension, etc. On continuous and constant exertion, the diabetic person is also liable for pancreatic fatigue. In addition, it is also seen that many of the existing drugs available lead to drug resistance in patients with long durations of use.

The long-term complications of diabetes are more damaging. This is caused by spikes in blood sugar in patients during the day. Increased blood sugar even for short periods leads to glycosylation of Hemoglobin. Glycosylated Hemoglobin causes long-term irreversible damages to eyes, kidneys, nerves and blood vessels.

A wide-spread pathological complication of Diabetes is thickening of capillary basement membrane, increase in vessel wall matrix and cellular proliferation resulting in vascular complications like lumen narrowing, early atherosclerosis, and sclerosis of glomerular capillaries, retinopathy, neuropathy and peripheral vascular insufficiency. The level of glycosylated hemoglobin (HbA1c) is also increased in diabetes and is taken as an index of protein glycosylation. It reflects the state of glycaemia over the preceding 2-3 months. As such, there is no drug available for the treatment of diabetic complications.

Further, diseases of the kidneys are very common now a days and it also occurs as complications or secondary to chronic diseases such as diabetes and heart diseases. Elevation of serum creatinine is a major parameter to identify the structural and functional health of the kidneys. There are no medicines available as on today which can improve the health of the defunct kidneys and thereby decrease the creatinine levels.

Diabetic eye disease refers to a group of eye problems that people with diabetes may face as a complication of diabetes. All can cause severe vision loss or even blindness.

Diabetic eye disease may include:

Diabetic retinopathy—damage to the blood vessels in the retina.

Cataract—clouding of the eye's lens. Cataracts develop at an earlier age in people with diabetes.

Glaucoma—increase in fluid pressure inside the eye that leads to optic nerve damage and loss of vision. A person with diabetes is nearly twice as likely to get glaucoma as other adults.

Diabetic retinopathy is the most common diabetic eye disease and a leading cause of blindness in American adults. It is caused by changes in the blood vessels of the retina. In some people with diabetic retinopathy, blood vessels may swell and leak fluid. In other people, abnormal new blood vessels grow on the surface of the retina. Blood vessels damaged from diabetic retinopathy can cause vision loss in two ways:

All people with diabetes—both type 1 and type 2—are at risk. The longer someone has diabetes, the more likely he or she will get diabetic retinopathy. Between 40 to 45 percent of pateints diagnosed with diabetes have some stage of diabetic retinopathy. Today, diabetic retinopathy is treated only with laser at the last stage of the disease. No medicine is available to manage and treat the same before such condition ensues.

Hypertension, also referred to as high blood pressure, is a medical condition in which the blood pressure is chronically elevated. In current usage, the word "hypertension" without a qualifier normally refers to systemic, arterial hypertension.

Persistent hypertension is one of the risk factors for strokes, heart attacks, heart failure and arterial aneurysm, and is a leading cause of chronic renal failure. Even moderate elevation of arterial blood pressure leads to shortened life expectancy. At severely high pressures, defined as mean arterial pressures 50% or more above average, a person can expect to live no more than a few years unless appropriately treated. Beginning at a systolic pressure of 115 mm Hg and diastolic pressure of 75 mm Hg (commonly written as 115/75 mm Hg), cardiovascular disease (CVD) risk doubles for each increment of 20/10 mm Hg.

All drug treatments for hypertension have side effects, and while the evidence of benefit at higher blood pressures is overwhelming, drug trials to lower moderately-elevated blood pressure have failed to reduce overall death rates.

Consequently, the need of the hour is to develop safe and efficacious drugs:
 i) that can help in the management of blood sugar levels and associated complications in diabetes mellitus patients. This drug should lend itself safe for long-term use without any side effects and without developing resistance.
 ii) that can help in the improving the renal health and thereby also reduce the elevated levels of serum creatinine. This drug should lend itself safe for long-term use without any side effects and without developing resistance.
 iii) that can help in prevention, management and treatment of diabetic retinopathy. This drug should lend itself safe for long-term use without any side effects and without developing resistance.
 iv) that can help in the management of hypertension and simultaneously act as a cardiac protective antioxidant. This drug should lend itself safe for long-term use without any side effects and without developing resistance.

PRIOR ART

For centuries, specific plants, their extracts or mixtures thereof have been used for treatment of illnesses in Indian system of medicine and many of them have been documented as having clinical effectiveness in treating diabetes. The plants like Alfalfa, Aloe Vera, Burdock, Celery, Comsilk, Damiana, Elecampane, *Eucalyptus*, Fenugreek, Garlic, Ginger, Ginseng, *Panax*, Juniper, Marshmallow, Myrrh, Nettle, Sage, Tansy which are all part of daily food ingredients have been also reported as hypoglycemic herbal ingredients.

Patent Application no. EP20050779434 teaches the invention provides an herbal composition comprising a plant extract from *Azadirachta indica*, Aloe vera and cinnamon, useful for the treatment of diabetes and type II diabetes associated complications such as atherosclerosis, hypertension, diabetic retinopathy, diabetic nephropathy, diabetic polyneuropathies, thyroid disorders, leg ulcers, diabetic foot and liver diseases, and for improving the immune function in a diabetic patient.

Patent Application no. KR20020011015 teaches An orient herbal medicinal formulation for the treatment of diabetes is provided. The formulation has especially curative and preventive effect for the insulin non-dependent diabetes (type 2 diabetes) and its complication as well as insulin dependent diabetes (type 1 diabetes) by lowering sugar content in the body. It also has excellent effect as a toner for the weak liver, kidney, stomach, lung and heart and as body stamina. CONSTITUTION: The formulation comprises: *Euonymus alatus* (Thumb) Sieb; balsam pear; *Lycium* root; corn filament; Salviae Radix; white *Atractylis; Curcuma longa* Rhizoma; white agaric; *Alisma; Cuscuta* seed; root peel of *Paeonia moutan* Sims in a weight ratio of 30:10:10:10:5:5:5:7:5:5:3, respectively. The cleaned *Euonymus alatus*. (Thumb) Sieb is put into distilled water and the solution is made pH 9 by adding NaOH, boiled under pressure for 3 hours, filtered, concentrated, dried under vacuum, ground and made powder by screening more than 100 times. The cleaned corn filament is fermented at 50 deg. C (with addition of yeast), separated from unwanted material, boiled under pressure with distilled water of 5 times for 3 hours, filtered, concentrated, dried under vacuum and made powder by screening more than 100 times. Salviae Radix is extracted with 70% ethanol, concentrated and dried under vacuum and made powder by screening more than 100 times. *Lycium* root, white *Atractylis, Curcuma longa* Rhizoma, white agaric, *Alisma* and *Cuscuta* seed and root peel of *Paeonia moutan* Sims are mixed, distilled water of 5 times is added, boiled 3 hours under vacuum, concentrated and dried under vacuum and made powder by screening more than 100 times. Balsam pear is obtained in liquid after freeze extracting and concentrating the filtrate. The above powders are mixed, screened more than 100 times, added to the concentrate of balsam pear and freeze dried to make the final formulation.

Patent application no. CA2532332 teaches an herbal extract-based composition comprising an extract of *Gynostemma pentaphyllum*, an extract of *Crataegus pinnatifidia* (hawthorn), an extract of *Camellia sinensis* (green tea), and an extract of *Momordica charantia* (bitter melon). The composition may further comprise an extract of mulberry (*Morus* species). Also provided is a process for preparing a herbal extract-based composition which comprises separately extracting each of hawthorn, green tea, *Gynostemma pentaphyllum*, mulberry, and bitter melon; drying extraction eluates obtained from the extracting of each of the herbal components to obtain organic residues in forming a hawthorn extract powder, green tea extract powder, a *Gynostemma pentaphyllum* extract powder, a mulberry extract powder, and a bitter melon powder; and combining the green tea extract powder, the *Gynostemma Pentaphyllum* extract powder, the hawthorn extract powder, the mulberry extract powder, and the bitter melon powder in desired proportions to form the herbal extract-based composition which, when taken orally, has health-promoting effects including anti-diabetic effects that include, but are not limited to, decreasing visceral fat, reducing hyperglycemia, and reducing the occurrence and severity of diabetic complications, associated with type 2 diabetes.

Patent application no WO02089825 teaches a herbal medicinal composition for preventing or treating type II diabetes. The composition is comprised of extracts from *Pterocarpus marsupium, Morus alba, Orthosiphon aristatus, Opiophogon japonicus, Rosa rugosa, Commelina communis, Trichosanthis kirilowii* and *Anemarrhena asphodeloides*.

The use of plant extracts and derivatives of plants for healing and prevention purposes has been described extensively in traditional and folk medicine literature. Over the centuries, plants have served as a major source of medicines for treating and prevention of diseases of mankind. Although recently the ability for synthesis and design of new medicines has provided new pathways for the development of therapeutic drugs; however, phytomedicines derived from plants still hold a strong position.

*Curcuma* has been used for lowering blood glucose level (Reference is made to the publication titled "Hyperglycemic activity of *Curcuma longa* of Tank, R.; Sharma, N.; Dixit, V. P. of the Reproductive Physiology Section, Department of Zoology, University of Rajasthan, Jaipur which appeared in the Indian Zoologist. v. 12(3-4): p. 321-322, 1988). It has also been reported that curcumin is more effective in attenuating diabetes mellitus than turmeric. (Reference is made to the publication titled "the Effect of turmeric on the enzymes of glucose metabolism in diabetic rats and published in the Journal of Herbs, Spices and Medicinal Plants. V. 10(1): p.

75-84, 2002 by Narayannasamy, A.; Namasivayam, N.; Radha, K. of the Department of Biochemistry, Annamalai University, Annamalainagar.

Reference is made to the publication by Arun, N.; Nalini, N. of the Department of Biochemistry, Annamalai University, Annamalainagar 608 002, Tamil Nadu, India titled the Efficacy of turmeric on blood sugar and polyol pathway in diabetic albino rats published in the Plant Foods for Human Nutrition. V. 57(1): p. 141-150, 2002 and which reads as "The effect of turmeric ([*Curcuma longa*]) rhizomes and its active principle, curcumin, on alloxan induced diabetes mellitus in a rat model was studied. Administration of turmeric or curcumin to diabetic rats reduced the blood sugar, Hb and glycosylated hemoglobin levels significantly. Turmeric and curcumin supplementation also reduced the oxidative stress encountered by the diabetic rats. This was demonstrated by the lower levels of TBRAS (thiobarbituric acid reactive substances), which may have been due to the decreased influx of glucose into the polyol pathway leading to an increased NADPH/NADP ratio and elevated activity of the potent antioxidant enzyme GPx. Moreover, the activity of SDH (sorbitol dehydrogenase), which catalyzes the conversion of sorbitol to fructose, was lowered significantly on treatment with turmeric or curcumin. These results also appeared to reveal that curcumin was more effective in attenuating diabetes mellitus related changes than turmeric.

Reference is made to the publication by Nalini, D.; Kapoor, R. Of the Department of Home Science, Sri Satya Sai Institute of Higher Learning, Anantapur, AP, India Titled Effect of plant fruits—Indian gall nut, bedda nut and gooseberry—on hypercholesterolemic rats and published by Plant Foods for Human Nutrition. v. 53(4): p. 343-349, 1999 which reads as The effect of supplementation of three fruits, [*Terminalia chebula*] (Indian gall nut), [*Terminalia belerica*], (bedda nut) and [*Emblica officinalis*] (gooseberry), on serum lipid levels and excretion of bile acids was investigated. Rats made hypercholesterolemic by feeding hypercholesterolemia inducing diet (HID) for a period of 30 days were used as the test model. Feeding of a dried powder of these fruits along with the HID resulted in significant (p less than 0.01) reduction in total cholesterol, LDL cholesterol and triglycerides. HDL cholesterol remained unchanged in groups fed gall nut and bedda nut. However, the levels were significantly (p less than 0.01) higher in groups fed mixed and gooseberry diets in comparison to the control diet. Excretion of bile acids was found to be significantly (p less than 0.01) higher in animals receiving the three fruits in combination in comparison to those receiving the individual fruits.

Reference is made to the publication by Dwivedi, S.; Gupta, D.; Sharma, K. K. of the Preventive Cardiology Group, UCMS and GTB Hospital, Delhi 110095, India titled the Modification of coronary risk factors by medicinal plants which appeared in the Journal of Medicinal and Aromatic Plant Sciences. v. 22(1B): p. 616-620, 2000 and reads as "Effect of four medicinal plants i.e. [*Terminalia arjuna, Emblica officinalis, Ocimum sanctum*] and [*Withania somnifera*] was examined. On risk factors in convalescing patients of coronary artery disease (myocardial infraction angina pectoris) was studied. The drug was adminsitered in a capsule form (Cardipro) in twice daily dosage. A total of 30 uncomplicated coronay artery disease patients were randomly divided into two groups A and B of 15 each. Group A patients were given Cardipro (1 Cap. BD) in addition to conventional antiischaemic therapy, while Group B patients were put on conventional regimen alone. Risk factor profile particularly lipids and left ventricular ejection fraction (LVEF) and left ventricular mass (LVM) of each subject were assessed before starting indigenous therapy and again after three months of therapy.

Administration of indigenous drugs resulted in significant reduction in systolic and diastolic blood pressure and elevation in HDL cholesterol was observed at the end of 3 months in the indigenous drug treated patients. About 6.7 percent of patients in Group A developed fresh ST-T changes as compared to 26.7 percent in the Group B. Significant improvement in LVEF and reduction in LVM were also noted."

Reference is made to the publication by Anila, L.; Vijayalakshmi, N. R. of the Department of Biochemistry, University of Kerala, Kariavattom, Trivandrum 695 581, Kerala, India and titled the Flavonoids from *Emblica officinalis* and *Mangifera indica*-effectiveness for dyslipidemia which appeared in the Journal of Ethnopharmacology. v. 79(1): p. 81-87, 2002 and reads as Flavonoids from [*Emblica officinalis*] and [*Mangifera indica*] effectively reduce lipid levels in serum and tissues of rats induced hyperlipidemia. Hepatic HMG CoA reductase activity was significantly inhibited in rats fed [*E. officinalis*] flavonoids. But increase of this enzyme was observed in rats administered [*M. indica*] flavonoids. The degradation and elimination of cholesterol was highly enhanced in both the groups. In [*E. officinalis*], the mechanism of hypolipidemic action is by the concerted action of inhibition of synthesis and enhancement of degradation. In the other group [*M. indica*] inhibition of cholesterogenesis was not encountered but significant degradation of cholesterol was noted, which may be the pivotal factor for hypolipidemic activity in this case. Though the mechanisms differ in the two cases, the net effect is to lower lipid levels."

Reference is made to the publication by Han, B. H.; Park, M. H.; Han, Y. N. of the Natural Products Research Institute, Seoul National University, Seoul 110-460, Korea titled the Sedative activity of aporphine and cyclopetide alkaloids isolated from the seeds of *Zizyphus vulgaris* var. *spinosus*, and the fruits and stem bark of *Zizyphus jujuba* var. *inermis* in mice which was published in the Yakhak Hoeji. v. 37(2): p. 143-148, 1993 and reads as The sedative activity of four aporphine alkaloids (APA) and nine cyclopeptide alkaloids (CPA), isolated from the seeds (sanjoin) of *Zizyphus vulgaris* var. *spinosus*] and the fruits and stem bark of [*Zizyphus jujuba* var. *spinosus*] and the fruits and stem bark of [*Zizyphus jujuba* var. *inermis*] has been reported. The assessment of sedative activity was carried out, employing a hexobarbital-induced sleeping time method in mice. When the relative sedative potency of sanjoinine-A (CAP) was given as one unit, those of nuciferine (APA), lysicamine (APA), chlorpromazine (positive control) and sanjoinine-Ahl (an epimer of sanjoinine-A) were 13, 6.5, 5, and 3 respectively. The sedative activities of other CPAs were much lower than those of sanjoinine-A and -Ahl, and other APAs were not active. On heat treatment, nuciferine and lysicamine were degraded into some artifacts which exhibited on sedative activity while sanjoinine-A was converted into sanjoinine-Ahl which showed more potent sedative activity. Nuciferine and sanjoinine-A were found to be major sedative components of native sanjoin, and that sanjoinine-A and its epimeric artifact, sanjoinine-Ahl were the active priniples of roasteanjoinine-A and its epimeric artifact, sanjoinine-Ahl were the active principles of roasted sanjoin. A scientific basis for heat-processing (roasting) of this Oriental medicine has been given.

Reference is made to the publication by Kim, T. H.; Yang, K. S.; Park, J. Y. of the College of Pharmacy, Sookmyung Women's University, Seoul 140-742, Korea titled the Effect of processed Cyperi Rhizoma on rat kidney function and published in Yakhak Hoeji. v. 42(1): p. 70-74, 1998 which reads as "[*Cyperus rotundus*] has been used as an analgesic, antiinflammatory agent, diuretic and emmenagogue in folk remedies. Cyperi Rhizomata, processed and unprocessed, were extracted with MeOH and fractionated with petroleum ether chloroform, butanol and water. In order to investigate the effects of their fractions on kidney function of acute renal failure rats induced by HgCl2, urinary volume, BUN, (blood urea nitrogen) creatinine, uric acid were determined. The diuretic effect of processed Cyperi Rhizoma was significantly increased in renal failure rats, on serum chemical parameters, the significant inhibition of BUN of processed Cyperi Rhizoma was revealed.

Reference is made to the publication by Sharma, S. R.; Dwivedi, S. K.; Swarup, D. of the Division of Medicine, Indian Veterinary Research Institute, Izatnagar 243 122, UP, India titled the Hypoglycaemic potential of *Mangifera indica* leaves in rats which appeared in the International Journal of Pharmacognosy. v. 35(2): p. 130-133, 1997 and which reads thus Hypoglycaemic activity of 50 percent ethanol extract of [*Mangifera indica*] tender leaves was studied in normal and streptozotocin induced diabetic rats. In normal rats, the extract was administered only once in doses of 100, 250 and 500 mg/kg per os. The highest decrease (37.73 percent) in plasma glucose levels was obtained with 250 mg dose after 8 h of administration. In diabetic rats, the extract produced significant antihyperglycaemic effect within 3 days when given at 250 mg/kg/day per os for 10 days. LD50 of the extract was above 4.64 gm/kg per os.

Reference is made to the publication by Teixeira, C. C.; Pinto, L. P.; Kessler, F. H. P.; Quadros da Paixao, L.; Miura, C. S.; Guimaraes, M. S.; Miura, M. S.; Gastaldo, G. J.; Fuchs, F. D. of the Departamento de Farmacologia da Universidad Federal do Rio Grande do Sul and Hospital de Clinicas de Porto Alegre, CEP 90 050 170 Porto Alegre, Brasil titled Is the decoction of mango leaves an antihyperglycemic tea? and which appeared in the Fitoterapia. v. 69(2): p. 165-168, 1998 and reads thus "The use of alternative therapies to treat diabetes, including teas prepared with different plants, is widespread in Brazil. An ethnopharmacological survey shows the prevalent use of a tea prepared with leaves of mango ([*Mangifera indica*]) by Brazilian diabetic patients. Therefore, the claimed hypoglycemic effect of this preparation has been investigated experimentally in normal rats and in streptozotocin-induced diabetic rats, and clinically in healthy volunteers. These results, showing no hypoglycemic effect of the treatment, strongly suggest that mango tea connot be recommended as an antidiabetic treatment."

Reference is made to the publication by Aderibigbe, A. O.; Emudianughe, T. S.; Lawal, B. A. S. of the Department of Pharmacology and Therapeutis University of Ilorin, Nigeria titled Antihyperglycaemic effect of *Mangifera indica* in rat which appeared in the Phytotherapy Research. v. 13(6): p. 504-507, 1999 and which reads thus "The effect of the aquoeus extract of [*Mangifera indica*] leaves on blood glucose level was assessed in normoglycaemic, glucose-induced hyperglycaemic and streptozotocin (STZ)-induced diabetic rats. The aqueous extract given orally (1 g/kg) did not alter the blood glucose levels in either normoglycaemic or STZ-induced diabetic rats. In glucose-induced hyperglycaemia, however, antidiabetic activity was seen when the extract and glucose were administered simultaneously and also when the extract was given to the rats 60 min before the glucose. The hypoglycaemic effect of the aqueous extract of the leaves of [*Mangifera indica*] has been attributed to an intestinal reduction of the absorption of glucose."

Reference is made to the following journal citations:

a) Diabetes Obesity and Metabolism. 2008 July; 10(7): 574-85

Faculty of Pharmacy, University of Sydney, Australia

*Salacia oblonga* root decreases cardiac hypertrophy in Zucker diabetic fatty rats: inhibition of cardiac expression of angiotensin II type 1 receptor.

AIMS: We investigated the effect of the water extract of *Salacia oblonga* (SOE), an ayurvedic antidiabetic and anti-obesity medicine, on obesity and diabetes-associated cardiac hypertrophy and discuss the role of modulation of cardiac angiotensin II type 1 receptor (AT(1)) expression in the effect. METHODS: SOE (100 mg/kg) was given orally to male Zucker diabetic fatty (ZDF) rats for 7 weeks. At the end-point of the treatment, the hearts and left ventricles were weighed, cardiomyocyte cross-sectional areas were measured, and cardiac gene profiles were analysed. On the other hand, angiotensin II-stimulated embryonic rat heart-derived H9c2 cells and neonatal rat cardiac fibroblasts were pretreated with SOE and one of its prominent components mangiferin (MA), respectively. Atrial natriuretic peptide (ANP) mRNA expression and protein synthesis and [(3)H]thymidine incorporation were determined. RESULTS: SOE-treated ZDF rats showed less cardiac hypertrophy (decrease in weights of the hearts and left ventricles and reduced cardiomyocyte cross-sectional areas). SOE treatment suppressed cardiac overexpression of ANP, brain natriuretic peptide (BNP) and AT(1) mRNAs and AT(1) protein in ZDF rats. SOE (50-100 microg/ml) and MA (25 micromol) suppressed angiotensin II-induced ANP mRNA overexpression and protein synthesis in H9c2 cells. They also inhibited angiotensin II-stimulated [(3) H]thymidine incorporation by cardiac fibroblasts. CONCLUSIONS: Our findings demonstrate that SOE decreases cardiac hypertrophy in ZDF rats, at least in part by inhibiting cardiac AT(1) overexpression. These studies provide insights into a potential cardioprotective role of a traditional herb, which supports further clinical evaluation in obesity and diabetes-associated cardiac hypertrophy.

b) Toxicology and Applied Pharmacology. 2006 Jan. 1; 210(1-2):78-85

Herbal Medicines Research and Education Centre, Faculty of Pharmacy, The University of Sydney, NSW 2006, Australia.

*Salacia oblonga* root improves cardiac lipid metabolism in Zucker diabetic fatty rats: modulation of cardiac PPAR-alpha-mediated transcription of fatty acid metabolic genes.

Excess cardiac triglyceride accumulation in diabetes and obesity induces lipotoxicity, which predisposes the myocytes to death. On the other hand, increased cardiac fatty acid (FA) oxidation plays a role in the development of myocardial dysfunction in diabetes. PPAR-alpha plays an important role in maintaining homeostasis of lipid metabolism. We have previously demonstrated that the extract from *Salacia oblonga* root (SOE), an Ayurvedic anti-diabetic and anti-obesity medicine, improves hyperlipidemia in Zucker diabetic fatty (ZDF) rats (a genetic model of type 2 diabetes and obesity) and possesses PPAR-alpha activating properties. Here we demonstrate that chronic oral administration of SOE reduces cardiac triglyceride and FA contents and decreases the Oil red O-stained area in the myocardium of ZDF rats, which parallels the effects on plasma triglyceride and FA levels. Furthermore, the treatment suppressed cardiac overexpression of both FA transporter protein-1 mRNA and protein in ZDF rats, suggesting inhibition of increased cardiac FA uptake as the basis for decreased cardiac FA levels. Additionally, the treatment also inhibited overexpression in ZDF rat heart of PPAR-alpha mRNA and protein and carnitine palmitoyltransferase- 1, acyl-CoA oxidase and 5'-AMP-activated protein kinase mRNAs and restored the downregulated acetyl-CoA carboxylase mRNA. These results suggest that SOE inhibits cardiac FA oxidation in ZDF rats. Thus, our findings suggest that improvement by SOE of excess cardiac lipid accumulation and increased cardiac FA oxidation in diabetes and obesity occurs by reduction of cardiac FA uptake, thereby modulating cardiac PPAR-alpha-mediated FA metabolic gene transcription.

c) Toxicology and Applied Pharmacology 2006 Feb. 1; 210(3):225-35

Herbal Medicines Research and Education Centre, Faculty of Pharmacy, The University of Sydney, NSW 2006, Australia

*Salacia oblonga* root improves postprandial hyperlipidemia and hepatic steatosis in Zucker diabetic fatty rats: activation of PPAR-alpha.

*Salacia oblonga* (SO) root is an Ayurvedic medicine with anti-diabetic and anti-obese properties. Peroxisome proliferator-activated receptor (PPAR)-alpha, a nuclear receptor, plays an important role in maintaining the homeostasis of lipid metabolism. Here, we demonstrate that chronic oral administration of the water extract from the root of SO to Zucker diabetic fatty (ZDF) rats, a genetic model of type 2 diabetes and obesity, lowered plasma triglyceride and total cholesterol (TC) levels, increased plasma high-density lipoprotein levels and reduced the liver contents of triglyceride, non-esterified fatty acids (NEFA) and the ratio of fatty droplets to total tissue. By contrast, the extract had no effect on plasma triglyceride and TC levels in fasted ZDF rats. After olive oil administration to ZDF the extract also inhibited the increase in plasma triglyceride levels. These results suggest that SO extract improves postprandial hyperlipidemia and hepatic steatosis in ZDF rats. Additionally, SO treatment enhanced hepatic expression of PPAR-alpha mRNA and protein, and carnitine palmitoyltransferase-1 and acyl-CoA oxidase mRNAs in ZDF rats. In vitro, SO extract and its main component mangiferin activated PPAR-alpha luciferase activity in human embryonic kidney 293 cells and lipoprotein lipase mRNA expression and enzyme activity in THP-1 differentiated macrophages; these effects were completely suppressed by a selective PPAR-alpha antagonist MK-886. The findings from both in vivo and in vitro suggest that SO extract functions as a PPAR-alpha activator, providing a potential mechanism for improvement of postprandial hyperlipidemia and hepatic steatosis in diabetes and obesity.

d) Life Sciences. 2004 Aug. 20; 75(14):1735-46

Herbal Medicines Research and Education Center, Faculty of Pharmacy A15, The University of Sydney, NSW 2006, Australia.

*Salacia oblonga* improves cardiac fibrosis and inhibits postprandial hyperglycemia in obese Zucker rats.

Diabetes has a markedly greater incidence of cardiovascular disease than the non-diabetic population. The heart shows a slowly developing increase in fibrosis in diabetes. Extended cardiac fibrosis results in increased myocardial stiffness, causing ventricular dysfunction and, ultimately, heart failure. Reversal of fibrosis may improve organ function survival. Postprandial hyperglycemia plays an important role in the development of type 2 diabetes and cardiovascular complications, and has been proposed as an independent risk factor for cardiovascular diseases. *Salacia oblonga* (S.O.) is traditionally used in the prevention and treatment of diabetes. We investigated the effects of its water extract on cardiac fibrosis and hyperglycemia in a genetic model of type 2 diabetes, the obese Zucker rat (OZR). Chronic administration of the extract markedly improved interstitial and perivascular fibrosis in the hearts of the OZR. It also reduced plasma glucose levels in non-fasted OZR, whereas it had little effect in the fasted animals, suggesting inhibition of postprandial hyperglycemia in type 2 diabetic animals, which might play a role in improvement of the cardiac complications of OZR. Furthermore, S.O. markedly suppressed the overexpression of mRNAs encoding transforming growth factor betas 1 and 3 in the OZR heart, which may be an important part of the overall molecular mechanisms. S.O. dose-dependently inhibited the increase of plasma glucose in sucrose-, but not in glucose-loaded mice. S.O. demonstrated a strong inhibition of alpha-glucosidase activity in vitro, which is suggested to contribute to the improvement of postprandial hyperglycemia.

e) Ahuja, G. L. Journal of the National Integrated Medical Association. v. 32(3): p. 9-11, 1990.

Role of Ayurvedic drugs-[*Terminalia arjuna, Boerhaavia diffusa, Commiphora mukul, Santalum album, Allium sativum, Terminalia chebula, Achyranthes aspera, Nardostachys, Aegle marmelos, Pirorhiza kurroa*], singly or in combination in curing hypertension, angina, cardiac failure, hypotension and cholesterolaemia has been discussed.

It has also been reported that the combinations of extracts of [*Curcuma longa*] and *Phyllanthus Emblica* exhibited good reduction in blood sugar level. Reference is made to the publication titled "Hypoglycaemic activity of *Curcuma longa* Linn. *Phyllanthus Emblica* Linn. And their various extractive combinations on albino rats" by Singh, A. K.; Chaudhary, R.; Manohar, S. J. of the College of Pharmacy, Push Vihar, New Delhi.

In the publication of Rajagopalan, K.; Sasidharnan, K. of the Keraleeya Ayurveda Samajam Hospital, Shoranur, Kerala, titled "The Evaluation of the clinical management of Prameha Roga (diabetes mellitus) which appeared in the Aryavaidyan. v. 14(1): p. 33-43, 2000 it has been stated that for the management of diabetes mellitus a formulation containing *Emblica officinalis, Curcuma longa, Tinospora cordifolia, Cyperus rotundus, Terminalia chebula, Syzygium cumini, Swertia chirata* etc can be used.

It is also reported in the publication of Bone, K. of the Medicinal Herba Private Limited, PO Box 713, Warwick 4370, Australia titled "the Turmeric—The spice of life" and published in the British Journal of Phytotherapy. V. 2(2): p. 51-60, 1991 that *curcuma longa* can be used for lowering cholesterol.

In the publication titled "Biologically active principles isolated from *Salacia oblonga* Wall" authored by Augusti, K. T.; Joseph, P. and Babu, T. D. of Amala Cancer Research Centre, Thrissur 680553, Kerala, which appeared in the Indian Journal of Physiology and pharmacology. V. 39(4): p. 415-417, 1995 discloses that two biologically active fractions have been isolated Salacia oblonga by chromatography. The chloroform eluted fraction by TLC demonstrated hypoglycemic potency of an equal dose of tolbutamide in albino rats.

In another publication titled Anti-peroxidative and hypoglycaemic activity of extract in diabetic rats authored by Krishnakumar, K.; Augusti, K. T.; Vijayammal, P. C. of the Department of Biochemistry, University of Kerala, which appeared in pharmaceutical Biology. V. 38(2): p. 101-105, 2000, it has been observed that the root bark of the herb possess antidiabetic and antiperoxidative activities and is useful in the treatment of diabetes and associated renal complications.

Prince, P. S. M.; Menon, V. P.; Pari, L. of the Department of Biochemistry, Annamalai University, Annamalai Nagar in their publication titled "Hypoglycaemic activity of Syzygium cumini seeds" which appeared in the Journal of Ethnopharmacology. v. 61(1): p. 1-7, 1998 have observed that Oral administration of the aqueous extract of the seed for 6 weeks resulted in a significant reduction in blood glucose and an increase in total haemoglobin.

In the publication of Jain, A. K.; Shaw, B. P. Research Department, Shree Visudanand Saraswati Marwari Hospital, Calcutta titled "Effect of herbal compound on maturity onset diabetes" which appeared in the Ancient Sci. Life. V. 7(1), p. 12-16, 1987 they have reported the antidiabetes effect of an herbal compound drug consisting of two herbs namely *Gymnema sylvestre* and *Sizygium cumini*.

Sharma, S. R.; Dwivedi, S. K.; Swarup, D. of the Division of Medicine, Indian Veterinary Research Institute, Izatnagar in their publication titled "the Hypoglycaemic potential of *Mangifera indica* leaves in rats" which appeared in the International Journal of Phramacognosy. v. 35(2): p. 130-133, 1997 have reported that 50 percent ethanol extract of *Mangifera indica* tender leaves significant anti-hyperglycaemic effect within 3 days.

Mahapatra, B. of the Dravyaguna, Gopabandhu Ayurveda Mahavidyalaya, Puri in their publication titled "the hypoglycaemic activity of *Coscinium fenestratum* (Gaertn.) Colebr" which appeared in the Journal of Research in Ayurveda and Siddha. v. 18(3-4): p. 89-96, 1997 have reported the significant hypoglycaemic activity.

In the publication of Ghosh, D.; Uma, R.; Thejomoorthy, P.; Veluchamy, G. of the Central Research Institute (Siddha), Arumbakkam, Madras titled "The Hypoglycaemic and toxicity studies of a combination of *Emblica* & *T. Chebula*" which appeared in the Journal of Research in Ayurveda and Siddha. v. 11(1-4): p. 78-89, 1990 have reported significant hypoglycaemic activity in fasting rabbits the drug was found to be non-toxic even when administered in high dose.

Puri, D.; Baral, N. of the Department of Biochemistry, B.P. Koirala Institute of Health Sciences, Dharan, Nepal in their publication titled "the Hypoglycaemic effect of [*Biophytum sensitivum*] in the alloxan diabetic rabbits" which appeared in the Indian Journal of Physiology and Pharmacology. V. 42(3): p. 401-406, 1998 have reported that that the plant material has significant antidiabetic effect.

In the publication of Mengi, S. A.; Deshpande, S. G. Of the C.U.S. College of Pharmacy, SNDT Women's University, Sir Vithaldas Vidya Vihar, Mumbai titled "An Assessment of ocular anti-inflammatory activity of roots and leaves of *Butea frondosa*: A histopathological study" published in British Journal of Phytotherapy. V. 5(2): p. 87-88, 1998 have revealed that *Butea frondosa*, topically applied, acted as an anti-inflammatory agent in experimentally induced inflammation of the eye.

Gupta, S.; Sanual, S. N.; Kanwar, U. Of the Department of Zoology, Punjab University, Chandigarh in their publication Titled "Effects of embelin, an antifertility agent, on the lipid metabolism of male albino rats" which appeared in the Fitoterapia. v. 60(4): p. 331-338, 1989 have observed that a benzoquinone isolated from *Embelia ribes*, revealed significant impairment in lipid metabolism.

Amin, K. M. Y.; Ahmed, S.; Khan, N. A. of the Department of Ilmul Advia, A. K. Tibbiya College, AMU Aligarh in their publication titled "Anti-nephrotic syndrome ethnic drug Bishiri Booti (*Aerva lanata*)—Experimental study of relevant pharmacological actions" presented at the Fourth Internat. Cong. Ethnobiol., NBRI, Lucknow. p. 94, 17-21 Nov. 1994 explains that [*A. lanata*], a wildly growing and cultivable herb of north India is used as a folk drug for renal and prostratic ailments. Though not described in standard texts of Unani Medicine, the drug is used by some Unani physicians for nephrotic syndrome.

In the publication of Khanna, A. K.; Chander, R.; Kapoor, N. K.; Singh, C.; Srivastava, A. K. Of the Division of Biochemistry, Central Drug Research Institute, Lucknow titled "Hypolipidemic activity of *Terminalia chebula* in rats" which Appeared in the Fitoterapia. V. 64(4): p. 351-356, 1993 have reported that the hypolipidemic action of the ethyl acetate soluble fraction of the alcoholic extract of [*T. chebula*] stem.

In the publication of Amirthaveni, M.; Vijayalakshmi, P.; Niklia, M. N. of the Department of Family and Community Science, Avinashilingam University, Coimbatore titled "Lipid profile of the heart patients and healthy volunteers and the effect of supplementation of Kadukkai (*Terminalia chebula*) on hypercholesterolemic patients" published by Indian Journal of Nutrition and Dietetics. v. 38(3): p. 83-88, 2001 reveals that [*Terminalia chebula*] (Kadukkai) has been found to possess cardio tonic and hypocholesterolemic effect.

In the publication by Awasthi, A. K.; Kothari, K.; Sharma, R. K. of the Department of Kayachikitsa, Rishikul State Ayurvedic College, Haridwar, UP, in their publication titled "Role of Haritakyadi vati in management of stable angina" Published by Aryavaidyan. v. 9(4): p. 214-219, 1996 have reported that Haritakivati (HT) is composed of seven herbal drugs such as *Terminalia chebula, Acorus calamus, Pluchea lanceolata, Piper longum, Zingiber officinale, Hedychium spicatum* and *Inula racemosa* and when Patients were administered 2 tablets of HT orally, the gradation of chest pain was found to be shifted towards less severe grades and anginal frequency was reduced. Reductions in serum cholesterol and serum triglyceride levels were significant.

Reference is made to the publication by Awasthi, A. K.; Kothari, K.; Sharma, R. K. Of the Department of Kayachikitsa, Rishikul State Ayurvedic College, Haridwar, UP, India Titled Role of Haritakyadi vati in management of stable angina Published by Aryavaidyan. v. 9(4): p. 214-219, 1996 And reads as Haritakivati (HT) is composed of seven herbal drugs such as [*Terminalia chebula, Acorus calamus, Pluchea lanceolata, Piper longum, Zingiber officinale, Hedychium spicatum*] and [*Inula racemosa*]. 20 Patients were administered 2 tablets of HT orally, TDS for 2 months and observations were made. The gradation of chest pain was found to be shifted towards less severe grades and anginal frequency was reduced. Reduction in serum cholesterol and serum triglyceride levels were significant. NSL, New Delhi.

Reference is made to the publication by Sood, R.; Sharma, A. K. Of the P.G. Department of Kayachikitsa, N.I.A., Japipur 302 002, Rajasthan, India Titled Effect of Bala Haritaki on hypercholesterolaemia And published in Journal of Research in Ayurveda & Siddha. v. 21(1-2): p. 11-18, 2000 which reads as Bala Haritaki [*Terminalia chebula*] was given to 15 subjects in the dose of 2 gm, twice a day in powdered form for 6 weeks with luke warm water. The results obtained showed statistically significant reduction in the level of serum cholesterol, serum triglycerides, total lipids, low density lipids, very low density lipids. There was a statistically significant increase in the level of high density lipids. However, there was no change in the body weight and adipose tissue thickness at the level of triceps, nape of neck and abdomen just below umblicus after therapy.

Reference is made to the publication by Ahirwar, B.; Singhai, A. K.; Dixit, V. K. Of the Department of Pharmaceutical Sciences, Dr. H. S. Gour University, Sagar 470 003, MP, India Titled as Effect of *Terminalia chebula* fruits on lipid profiles of rats And published by Journal of Natural Remedies. v. 3(1): p. 31-35, 2002 Which reads as The ethanolic extract and ethyl acetate fractions of [*Terminalia chebula*] fruits were found to possess significant hypolipidaemic activity. The most active extract of [*T. chebula*] is ethyl acetate fraction of immature fruits, which was able to bring high serum lipid to normal level.

Reference is made to the publication by Ahirwar, B.; Singhai, A. K.; Dixit, V. K.* Of the Department of Pharmaceutical Sciences, Dr. H. S. Gour University, Sagar 470 003, Madhya Pradesh, India Titled the Effect of *Terminalia chebula* fruits on lipid profiles of rats And published by Journal of Natural Remedies. v. 3(1): p. 31-35, 2003 Which reads as In atherogenic diet induced hyperlipidemic model, the rats receiving alcoholic extract of immature (IMF), mature (MF) fruits and ethyl acetate soluble fraction (immature fruits) of [*Terminalia chebula*] treatment showed marked reduction in total cholesterol (TC), total triglyceride (TG), total protein (TP) and elevation. in high density lipoprotein cholesterol (HDL-C). In normocholesterolemic model, the feeding of ethanolic extract (immature fruits) lowered the levels of TC, TG, TP and increased level of HDL-C. The most active extract of [*T. chebula*] is ethyl acetate fraction of immature fruits, which was able to bring high serum lipid to normal level.

Reference is made to the publication by Mand, J. K.; Soni, G. L.; Gupta, P. P.*; Rattan Singh of the Department of Biochemistry, Punjab Agricultural University, Ludhiana 141 004, Punjab, India titled Effect of Amla (*Emblica officinalis*) on the development of atherosclerosis on hypercholesterolemic rabbits which appeared in the Journal of Research and Education in Indian Medicine. v. 10(2): p. 1-7, 1991 and reads thus "Feeding of Amla to the hypercholesterolemic rabbits for 12 weeks showed a two prong effect, its feeding increased the lipid mobilization and catabolism and retarded the deposition of lipids in the extrahepatic tissues.

Feeding of [*E. officianalis*] initially raised the plasma lipids and cholesterol levels but by the end of 12 weeks, their levels were reduced significantly below the levels in the control group. Lipid levels of liver were also significantly lowered. Though lipid levels of aorta increased during this period but the increase was much less in Amla fed animals as compared to the control group. The degree of atherosclerosis at the end of 12 weeks of Amla feeding was lower as compared to that in the control group."

Reference is made to the publication by Mathur, R.; Sharma, A.; Dixit, V. P.; Verma, M. of the Department of Zoology, University of Rajasthan, Jaipur 302004 Rajasthan, India titled the Hypolipidaemic effect of fruit juice of *Emblica officinalis* in cholesterol-fed rabbits published in the Journal of Ethnopharmacology. v. 50(2): p. 61-68, 1996 and which reads thus "[*Emblica officinalis*] juice was administered at a dose of 5 ml/kg body weight per rabbit per day for 60 days. Serum cholesterol, TG, phospholipid and LDL levels were lowered by 82 percent, 66 percent, 77 percent and 90 percent, respectively. Similarly, the tissue lipid levels showed a significant reduction following [*E. officinalis*] juice administration. Aortic plaques were regressed. [*E. officinalis*] juice treated rabbits excreted more cholesterol and phospholipids, suggesting that the mode of absorption was affected. [*E. officinalis*] juice is an effective hypolipidaemic agent and can be used as a pharmaceutical tool in hyperlipidaemic subjects."

Han, B. H.; Park, M. H.; Han, Y. N. of the Natural Products Research Institute, Seoul, Korea in their publication titled "Activity of aporphine and cyclopetide alkaloids isolated from the seeds of *Zizyphus vulgaris* var. *spinosus*, and the fruits and stem bark of *Zizyphus jujuba* var. *inermis* in mice" which was published in the Yakhak Hoeji. v. 37(2): p. 143-148, 1993 have reported the sedative activity of the herb.

It is known from the publication of Kim, T. H.; Yang, K. S.; Park, J. Y. of the College of Pharmacy, Sookmyung Women's University, Seoul 140-742, Korea in their publication titled "The Effect of processed Cyperi Rhizoma on rat kidney function" published in Yakhak Hoeji. v. 42(1): p. 70-74, 1998 which reads as [*Cyperus rotundus*] that the herb has been used as an analgesic, anti-inflammatory agent, diuretic and emmenagogue in folk remedies.

In the publication of Chatterjee, T. K.; Chakraborty, A.; Pathak, M. Of the Pharmacology Research Laboratory, Department of Pharmaceutical Technology, Jadavpur University, Calcutta titled as "Effects of plant extract *Centella asiatica* (Linn.) On cold restraint stress ulcer in rats" published by Indian Journal of Experimental Biology. v. 30(10): p. 889-891, 1992 reveals that the Extract of [*C. asiatica*] inhibited significantly gastric ulceration induced by cold and restraint stress (CRS) in rats.

The prior arts described above, indicate that some studies have been carried out into effectiveness of the various herbs individually, in the management of diabetes and other separate health conditions such as hyper-tension, hyper-cholesterolemia and impaired cardiac, renal or ocular health. But no information is available in respect of a herbal combination which has a combined effect as a health protective, promotive and disease preventive for diabetics that is safe for long term use and having significant combined medicinal values such as reduction of hyperglycemia, reduction in hypoglycemic dependency and improvement in the general health of diabetics patients along with prevention and management of many of the complications arising from diabetes. In other words, no prior art knowledge is available where the specific combination of various herbs is useful for treating simultaneously diabetes and the associated disease conditions such as higher than normal levels of glycosylated hemoglobin, serum creatinine, serum total cholesterol, serum LDL, serum VLDL and serum Triglycerides as well as lower than normal levels of serum HDL cholesterol, numbness and pain in the limbs, constipation and disturbed sleep arising as a part of the wrong metabolic processes of diabetes.

The use of plant extracts and derivatives of plants for healing and prevention purposes has been described extensively in traditional and folk medicine literature. Over the centuries, plants have served as a major source of medicines for treating and prevention of diseases of mankind. Although recently the ability for synthesis and design of new medicines has provided new pathways for the development of therapeutic drugs; however, phytomedicines derived from plants still hold a strong position.

OBJECT OF THE INVENTION

The main object of the invention is to provide a safe and effective herbal formulation and a process for preparing the same, which prevents and treats diabetes and associated complications of diabetes.

Another object of the present invention is to provide a safe and effective herbal formulation and a process for preparing the same, which improves the renal function and health of the diabetics, reduces the elevated levels of serum creatinine, decreases the incidence of urinary tract infections and offers better quality of life to the diabetic patients.

Yet another object of the invention is to provide a safe and effective herbal formulation and a process for preparing the same, which prevent the damages to the ophthalmic blood vessels and also prevents and treatments retinopathy associated with diabetes.

Another object of the present invention is to provide a safe and effective herbal composition and a process for preparing the same, which improves the cardiovascular health of diabetic patient and reduces hypertension, improves the ratio of the serum lipid profile and improves cardiac functional parameters of a diabetic patient.

Still another object of the present invention is to provide a safe and effective herbal formulation and a process for preparing the same, which reduces the pain and numbness associated with peripheral neuropathy, improves wound healing of diabetic ulcers, improves bowel evacuation and sleep and generally improves the quality of life of the diabetic patient.

Yet another objective of the present invention is to provide a safe and effective herbal formulation which is processed as a synergestic herbal compound powder or fermented herbal nutraceutical beverage or high-fiber nutraceutical food stuff(s) or extract/concentrate which is further formulated using known conventional processes to tablets or capsules or granules or syrups or herbal health drink or inhalable herbal medicinal preparations or ocular preparations or transdermal absorbable preparations such as ointments/gels or injectable medicine. In occasions of the extract/concentrate being further formulated, the formulation may also optionally contain suitable digestive, flavoring, binding, sweetening and excieipent and/or absorptive adjuvants which are normally used in such formulations, as per the particular requirements.

SUMMARY OF THE INVENTION

The ingredient herbs of the herbal formulation for the treatment and prevention of diabetes and other associated complications are:
- a) The Species *Emblica* of *officinalis* Gaertn. (Synonym: *Phyllanthus emblica* L.) of the Euphorbiaceae Family,
- b) The Species of herbs of the Genus *Salacia* of the of the Celastraceae family,
- c) The Species *Strychnos potatorum* L. f. of the Strychnaceae family,
- d) The Species *Vetiveria zizanioides* (L.) Nash (Synonym: *Andropogon squarrosus* Hook f. (non L. f.) of the Poaceae family,
- e) The Species *Curcuma longa* L. of the Zingiberaceae family,
- f) The Species of herbs of the Genus *Aerva* of the Amaranthaceae family,
- g) The Species of herbs of the Genus *Biophytum* of the Oxalidaceae family,
- h) The Species of herbs of the Genus *Syzygium* of the Myrtaceae family
- i) The Species *Mangifera indica* L. of the Anacardiaceae family,
- j) The Species of herbs of the Genus *Cyclea* and/or the Genus *Cissampelos* of the Menispermaceae family,
- k) The Species of herbs of the Genus *Embelia* of the Myrsinaceae family,
- l) The Species of herbs of the Genus *Cyperus* of the Cyperaceae family,
- m) The Species *Terminalia chebula* (Gaertn.) Retz. of the Combretaceae family,
- n) The Species *Centella asiatica* (L.) Urban of the Apiaceae family and/or the Species *Strychnos nux-vomica* L. (Synonym: *Strychnos ligustrina* Blume) of the Strychnaceae family, and/or the Species *Butea frondosa* Koen. ex Roxb. (synonym: *Butea monosperma* (Lam.) Taub. of the Papilionaceae family and/or the Species *Acacia catechu* (L.f.) Willd. of the Mimosaceae family,
- o) The Species *Coscinium fenestratum* (Gaertn.) Colebr. of the Menispermaceae family and/or the Species of herbs of the Genus *Berberis* of the Berberidaceae family, and
- p) The species of herbs of the Genus *Zizyphus* of the Rhamnaceae family.

The ingredient herbs of the formulation for prevention and treatment of diabetes are:
- a) The Species *Emblica officinalis* Gaertn. (Synonym: *Phyllanthus emblica* L.) of the Euphorbiaceae Family,
- b) The Species of herbs of the Genus *Salacia* of the of the Celastraceae family,
- c) The Species *Curcuma longa* L. of the Zingiberaceae family,
- d) The Species of herbs of the Genus *Syzygium* of the Myrtaceae family,
- e) The Species *Mangifera indica* L. of the Anacardiaceae family, and
- f) The Species of herbs of the Genus *Cyclea* and/or roots of the Genus *Cissampelos* of the Menispermaceae family.

The ingredient herbs of the formulation for prevention and treatment of renal complications associated with diabetes are:
- a) The Species *Strychnos potatorum* L. f. of the Strychnaceae family,
- b) The Species *Vetiveria zizanioides* (L.) Nash (Synonym: *Andropogon squarrosus* Hook f. (non L. f.) of the Poaceae family,
- c) The Species of herbs of the Genus *Aerva* of the Amaranthaceae family,
- d) The Species of herbs of the Genus *Cyclea* and/or the Genus *Cissampelos* of the Menispermaceae family and
- e) The Species of herbs of the Genus *Cyperus* of the Cyperaceae family.

The ingredient herbs of the formulation for prevention and treatment of retinopathy associated with diabetes are:
- a) The Species *Emblica officinalis* Gaertn. (Synonym: *Phyllanthus emblica* L.) of the Euphorbiaceae Family,
- b) The Species *Strychnos potatorum* L. f. of the Strychnaceae family,
- c) The Species *Curcuma longa* L. of the Zingiberaceae family, and
- d) The Species *Coscinium fenestratum* (Gaertn.) Colebr. of the Menispermaceae family and/or the Species of herbs of the Genus *Berberis* of the Berberidaceae family.

The ingredient herbs of the formulation for prevention and treatment of oxidative damage to heart and its blood vessels associated with diabetes are:
- a) The Species of herbs of the Genus *Salacia* of the of the Celastraceae family,
- b) The Species *Mangifera indica* L. of the Anacardiaceae family,
- c) The Species of herbs of the Genus *Cyperus* of the Cyperaceae family,
- d) The Species *Terminalia chebula* (Gaertn.) Retz. of the Combretaceae family, and
- e) The Species of herbs of the Genus *Zizyphus* of the Rhamnaceae family.

The list of preferred herbs in any of the preceeding five formulations, wherein the species is not specified but only the genus is described:

In any of the preceeding five formulations, wherein the Species of the Genus *Salacia* of the Celastraceae family are mentioned the following herbs needs to be utilized: *Salacia oblonga* Wall. ex Wight & Arn. and/or, *Salacia reticulata* Wight and/or, *Salacia chinensis* L. (Synonym: *Salacia latifolia* Wall. ex. Laws; *Salacia prinoides* DC.) and/or *Salacia fruticosa* Heyne, and/or *Salacia macrosperma* Wight.

In any of the preceeding five formulations, wherein the Species of the Genus *Aerva* of the Amaranthaceaea family are mentioned the following herbs needs to be utilized: *Aerva*

*lanata* Juss., and/or *Aerva javanica* (Burm. f.) Juss. ex J. A. Schultes (Synonym: *Aerva tomentosa* Forsk., *Aerva persica* (Burm. f.) Merrill).

In any of the preceeding five formulations, wherein the Species of the Genus *Biophytum* of the Oxalidaceae family are mentioned the following herbs needs to be utilized: *Biophytum sensitivum* (L.) DC. (Synonym: *Oxalis sensitivum* L.) and/or *Biophytum reinwardtii* Edgw. & Hk. f.

In any of the preceeding five formulations, wherein the the Species of the Genus *Syzygium* of the Myrtaceae family are mentioned the following herbs needs to be utilized: *Syzygium cumini* (L.) Skeels (Synonym: *Eugenia jambolana* Lam.) and/or *Syzygium caryophyllaeum* Gaertn. (Synonym: *Eugenia carophyllaea* Wt.).

In any of the preceeding five formulations, wherein the Species of the Genus *Cyclea* or Species of the Genus *Cissampelos* of the Menispermaceae family are mentioned the following herbs needs to be utilized respectively: *Cyclea peltata* (Lam.) Hook. f. & Thorns. and/or *Cissampelos pareira* L.

In any of the preceeding five formulations, wherein the Species of the Genus *Embelia* of the Myrsinaceae family are mentioned the following herbs needs to be utilized: *Embelia ribes* Burm. f. and/or *Embelia tsjerium-cottam* A. DC. (Synonym: *Embelia robusta* Clarke (non Roxb.).

In any of the preceeding five formulations, wherein the Species of the Genus *Cyperus* of the Cyperaceae family are mentioned the following herbs needs to be utilized: *Cyperus rotundus* L., (Synonym: *Cyperus rotundus* L. ssp. *tuberosus* (Rottb.) Kuekenth; and *Cyperus tuberosus* Rottb.) and/or *Cyperus esculentus* L. and/or *Cyperus scariosus* R. Br.

In any of the preceeding five formulations, wherein the Species of the Genus *Berberis* of the Berberidaceae family are mentioned the following herbs needs to be utilized: *Berberis aristata* DC. var. *aristata* (Synonym: *Berberis aristata* Hook. f. & Thorns., *Berberis chitria* Lindl.) and/or *Berberis calliobotrys* Aitch. ex Koehne and/or *Berberis lycium* Royle and/or *Berberis orthobotrys* Bien. ex. Aitch. and/or *Berberis umbellata* Wall. ex G. Don. and/or *Berberis vulgaris* L.

In any of the preceeding five formulations, wherein the Species of the Genus *Zizyphus* of the Rhamnaceae family are mentioned the following herbs needs to be utilized: *Zizyphus jujuba* Lamk. (Synonym: *Zizyphus mauritiana* Lamk.), and/or *Zizyphus xylopyrus* (Retz.) Willd. (xylopyra, xylophora) and/or *Zizyphus jujuba* Mill. (Synonym: *Zizyphus sativa* Gaertn., *Zizyphus vulgaris* Lamk.) and/or *Zizyphus oenoplia* (L.) Mill. and/or *Zizyphus rugosa* Lamk., and/or *Zizyphus glabrata* Heyne ex Roth and/or *Zizyphus nummularia* (Burm. f.) Wt. & Arn.

The preferred species of herbs to be used as ingredients in the formulation for the treatment and prevention of diabetes and other associated complications are:
 a) *Emblica officinalis* Gaertn. (Synonym: *Phyllanthus emblica* L.) of the Euphorbiaceae Family,
 b) *Salacia oblonga* Wall. ex Wight & Arn. of the of the Celastraceae family,
 c) *Strychnos potatorum* L. f. of the Strychnaceae family,
 d) *Vetiveria zizanioides* (L.) Nash (Synonym: *Andropogon squarrosus* Hook f. (non L. f.) of the Poaceae family,
 e) *Curcuma longa* L. of the Zingiberaceae family,
 f) *Aerva lanata* Juss of the Amaranthaceae family,
 g) *Biophytum sensitivum* (L.) DC. (Synonym: *Oxalis sensitivum* L.) of the Oxalidaceae family,
 h) *Syzygium cumini* (L.) Skeels (Synonym: *Eugenia jambolana* Lam.) of the Myrtaceae family
 i) *Mangifera indica* L. of the Anacardiaceae family,
 j) *Cyclea peltata* (Lam.) Hook. f. & Thorns. of the Menispermaceae family,
 k) *Embelia ribes* Burm. f. of the Myrsinaceae family,
 l) *Cyperus rotundus* L., (Synonym: *Cyperus rotundus* L. ssp. *tuberosus* (Rottb.) Kuekenth; and *Cyperus tuberosus* Rottb.) of the Cyperaceae family,
 m) *Terminalia chebula* (Gaertn.) Retz. of the Combretaceae family,
 n) *Centella asiatica* (L.) Urban of the Apiaceae family
 o) *Coscinium fenestratum* (Gaertn.) Colebr. of the Menispermaceae family, and
 p) *Zizyphus jujuba* Lamk. (Synonym: *Zizyphus mauritiana* Lamk.) of the Rhamnaceae family.

The preferred species of herbs to be used as ingredients in the formulation for the prevention and treatment of diabetes are:
 a) *Emblica officinalis* Gaertn. (Synonym: *Phyllanthus emblica* L.) of the Euphorbiaceae Family,
 b) *Salacia oblonga* Wall. ex Wight & Arn. of the of the Celastraceae family,
 c) *Curcuma longa* L. of the Zingiberaceae family,
 d) *Syzygium cumini* (L.) Skeels (Synonym: *Eugenia jambolana* Lam.) of the Myrtaceae family
 e) *Mangifera indica* L. of the Anacardiaceae family, and
 f) *Cyclea peltata* (Lam.) Hook. f. & Thorns. of the Menispermaceae family, The preferred species of herbs to be used as ingredients in the formulation for the prevention and treatment of renal complications associated with diabetes are:
 a) *Strychnos potatorum* L. f. of the Strychnaceae family,
 b) *Vetiveria zizanioides* (L.) Nash (Synonym: *Andropogon squarrosus* Hook f. (non L. f.) of the Poaceae family,
 c) *Aerva lanata* Juss of the Amaranthaceae family,
 d) *Cyclea peltata* (Lam.) Hook. f. & Thorns. of the Menispermaceae family, and
 e) *Cyperus rotundus* L., (Synonym: *Cyperus rotundus* L. ssp. *tuberosus* (Rottb.) Kuekenth; and *Cyperus tuberosus* Rottb.) of the Cyperaceae family, The preferred species of herbs to be used as ingredients in the formulation for the prevention and treatment of retinopathy associated with diabetes are:
 a) *Emblica officinalis* Gaertn. (Synonym: *Phyllanthus emblica* L.) of the Euphorbiaceae Family,
 b) *Strychnos potatorum* L. f. of the Strychnaceae family,
 c) *Curcuma longa* L. of the Zingiberaceae family, and
 d) *Coscinium fenestratum* (Gaertn.) Colebr. of the Menispermaceae family, The preferred species of herbs to be used as ingredients in the formulation for prevention and treatment of oxidative damage to heart and its blood vessels, associated with diabetes are:
 a) *Salacia oblonga* Wall. ex Wight & Arn. of the of the Celastraceae family,
 b) *Mangifera indica* L. of the Anacardiaceae family,
 c) *Cyperus rotundus* L., (Synonym: *Cyperus rotundus* L. ssp. *tuberosus* (Rottb.) Kuekenth; and *Cyperus tuberosus* Rottb.) of the Cyperaceae family,
 d) *Terminalia chebula* (Gaertn.) Retz. of the Combretaceae family, and
 e) *Zizyphus jujuba* Lamk. (Synonym: *Zizyphus mauritiana* Lamk.) of the Rhamnaceae family.

Any one or any few or all parts of the above plants, processed in any form may be used in the formulation, with varying degrees of effectiveness. The formulation shall give the most desired and optimum results of clinical efficacy and safety, when the following parts of the preferred ingredient plants are used:

a) Fruits without the seeds of *Emblica officinalis* Gaertn. (Synonym: *Phyllanthus emblica* L.) of the Euphorbiaceae Family,
b) Roots of *Salacia oblonga* Wall. ex Wight & Arn. of the of the Celastraceae family,
c) Seeds of *Strychnos potatorum* L. f. of the Strychnaceae family,
d) Fibrous roots of *Vetiveria zizanioides* (L.) Nash (Synonym: *Andropogon squarrosus* Hook f. (non L. f.) of the Poaceae family,
e) Rhizomes of *Curcuma longa* L. of the Zingiberaceae family,
f) Whole plant of *Aerva lanata* Juss of the Amaranthaceae family,
g) Whole plant of *Biophytum sensitivum* (L.) DC. (Synonym: *Oxalis sensitivum* L.) of the Oxalidaceae family,
h) Seeds of *Syzygium cumini* (L.) Skeels (Synonym: *Eugenia jambolana* Lam.) of the Myrtaceae family
i) Seed kernels of *Mangifera indica* L. of the Anacardiaceae family,
j) Tuberous roots of *Cyclea peltata* (Lam.) Hook. f. & Thorns. of the Menispermaceae family,
k) Fruits/Seeds of *Embelia ribes* Burm. f. of the Myrsinaceae family,
l) Rhizomes of *Cyperus rotundus* L., (Synonym: *Cyperus rotundus* L. ssp. *tuberosus* (Rottb.) Kuekenth; and *Cyperus tuberosus* Rottb.) of the Cyperaceae family,
m) Fruits without seeds of *Terminalia chebula* (Gaertn.) Retz. of the Combretaceae family,
n) Whole plant of *Centella asiatica* (L.) Urban of the Apiaceae family
o) Stem with bark of *Coscinium fenestratum* (Gaertn.) Colebr. of the Menispermaceae family, and
p) Fruits with seeds and stem bark of *Zizyphus jujuba* Lamk. (Synonym: *Zizyphus mauritiana* Lamk.) of the Rhamnaceae family.

Preparation of preferred parts of the herbal raw materials for herbal formulation for the treatment and prevention of diabetes and other associated complications are:

a) *Emblica officinalis* Gaertn: Fresh fruits of *Emblica officinalis* Gaertn are collected and cleaned well with water to remove any impurities. The fruits are then wiped dry and cut to two pieces, longitudinally, to the point of attachment of the fruit stalk. The seeds are removed and the fruit pulp is dried so as not to expose the fruit pulp to direct sun-light. The dried fruit pulp is powdered in pulverizes of mesh size between 5 millimeters and then and 3 millimeters, to get a homogenous powder of average particle size of 1 millimeter to 3 millimeters.
b) *Salacia oblonga* Wall. Ex Wight & Arn.: Fresh roots of the plant *Salacia oblonga* Wall. Ex Wight & Arn are collected and washed in water to remove external impurities. The they are cut into longitudinal pieces of 1 to 1.5 inches length and again washed well with water. The clean pieces are dried in mild direct sunlight and then further cut into smaller pieces of 1 to 1.5 centimeters length. These pieces are pulverized using mesh size of 5 millimeter, first and then using 3 millimeter, after that, to yield a homogenous powder of average particle size of 1 millimeter to 3 millimeters.
c) *Strychnos potatorum* L. f.: Dried and dispersible seeds of *Strychnos potatorum* L. f are collected and washed well for clearing the physical impurities. The seeds are then dried in good sunlight and further fried in dry heat in a shallow bottom iron frying pan at around 60 to 75 degree Celsius. The fried seeds are pulverized using 5 millimeter mesh size and further 3 millimeter mesh size to yield a homogenous powder of average particle size of 1 millimeter to 3 millimeters.
d) *Vetiveria zizanioides* (L): The fibrous roots of freshly unearthed *Vetiveria zizanioides* (L) plants are cut off from the shoot, leaving a gap of 1.5 to 2 centimeters. The roots are then washed off the sand and other physical impurities using water and dried in shade and low humidity. The roots when semi dried are further cut into smaller pieces of not more than 2 centimeters long. The cut roots are further dried fully and pulverized using 3 millimeter mesh size to yield a homogenous powder of average particle size of 1 millimeter to 3 millimeters.
e) *Curcuma longa* L.: The rhizomes of *Curcuma longa* L. are collected and washed off the physical impurities with boiling water and dried under shade. The dried rhizomes are as such fed into the pulveriser with a 5 millimeter mesh size and further a 3 millimeter mesh size to yield a homogenous powder of average particle size of 1 millimeter to 3 millimeters.
f) *Aerva lanata* Juss.: The whole herb of *Aerva lanata* Juss are collected including the root and shoot system completely. The plant is washed and cut into pieces of 1.5 to 2 centimeters length. The cut plant parts are further dried fully in shade and pulverized using 3 millimeter mesh size to yield a homogenous powder of average particle size of 1 millimeter to 3 millimeters.
g) *Biophytum sensitivum* (L) DC.: The whole herb of *Biophytum sensitivum* (L) DC., are collected including the root and shoot system completely. The plant is washed and cut into pieces of 1.5 to 2 centimeters length. The cut plant parts are further dried fully in shade and pulverized using 3 millimeter mesh size to yield a homogenous powder of average particle size of 1 millimeter to 3 millimeters.
h) *Syzygium cumini* (L) Skeels: Fresh ripe fruits of *Syzygium cumini* (L) Skeels are collected and the fruit pulp is scraped of with rough cloth to leave the seeds completely exposed. The seeds are further kept in warm water of 40 to 45 degree Celsius for 10 minutes and then it is further wiped dried to remove all traces of water and any adhering fruit pulp. The seed is further dried in shade and pulverized using 3 millimeter mesh size to yield a homogenous powder of average particle size of 1 millimeter to 3 millimeters.
i) *Mangifera indica* L.: Fresh ripe fruits of *Mangifera indica* L are collected and the seeds are cleaned off the fruit pulp. The seeds are further dried well in good sunlight. The dried seeds are cut into two using very sharp pliers and the seed coat and seed kernel are separated. The seed coats are discarded and seed kernels are further dried in direct sunlight and the kernel are pulverized using 3 millimeter mesh size to yield a homogenous powder of average particle size of 1 millimeter to 3 millimeters.
j) *Cyclea peltata* (Lamk.) Hook. f & Thoms.: The fresh tuberous roots of *Cyclea peltata* (Lamk.) Hook. f & Thorns are collected giving care not to lose any of the long running roots, left in the soil. The roots are then washed well with water to remove physical impurities and dried in direct sunlight. The dried tuberous roots are then cut into small pieces of 1.5 to 2 centimeters length and further dried in direct sunlight. These small pieces of *Cyclea peltata* (Lamk.) Hook. f & Thorns roots are pulverized using 3 millimeter mesh size to yield a homogenous powder of average particle size of 1 millimeter to 3 millimeters.

k) *Embelia ribes* Burm. f: The ripe berries of *Embelia ribes* Burm. f are collected and hand picked to sort out the physical impurities. The rest of the berries are washed well to further clean them and then dried in direct sunlight after spreading the berries into a thin layer. The well dried berries are then pulverized using 3 millimeter mesh size to yield a homogenous powder of average particle size of 1 millimeter to 3 millimeters.

l) *Cyperus rotundus* L.: The fresh rhizomes of *Cyperus rotundus* L are collected and the rhizomes are cut off from the base of the shoot 0.25 to 0.5 centimeters and washed well in water to remove all physical impurities. Care must be taken to use water jet with pressure to remove all the soil particles which usually gets entangled in the rootlets and root hairs which arise from the rhizomes. The washed rhizomes are then dried direct sun light for a day to remove the moisture of washing and then the rhizomes are cut into 2 pieces to expose the raw white cut surface. The rhizomes are then further dried in shade to remove maximum moisture from them and then are pulverized using 3 millimeter mesh size to yield a homogenous powder of average particle size of 1 millimeter to 3 millimeters.

m) *Terminalia chebula* (Gaertn.) Retz.: Fresh fruits of *Terminalia chebula* (Gaertn.) Retz are collected and cleaned well with water to remove any impurities. The fruits are then wiped dry and cut to two pieces, longitudinally, to the point of attachment of the fruit stalk. The seeds are removed and the fruit pulp is dried so as not to expose the fruit pulp to direct sun-light. The dried fruit pulp is powdered in pulverizers of mesh size between 5 millimeters and then and 3 millimeters, to get a homogenous powder of average particle size of 1 millimeter to 3 millimeters.

n) *Centella asiatica* (L) Urban.: The whole herb of *Centella asiatica* (L) Urban, are collected including the root and shoot system completely. The plant is washed and cut into pieces of 1.5 to 2 centimeters length. The cut plant parts are further dried fully in shade and pulverized using 3 millimeter mesh size to yield a homogenous powder of average particle size of 1 millimeter to 3 millimeters.

o) *Coscinium fenestratum* (Gaertn.) Colebr.: The stem of *Coscinium fenestratum* (Gaertn.) Colebr are cut from a branch which has more than 3 months of growth. Care is taken to retrieve the entire length of the stem so as to minimize the eco-system impact per kilogram of the raw material used. The stem is washed well with water, taking precaution, not to shear of any bark, and dried in direct sunlight. The dried stem is then cut cross sectional, so that each cylindrical piece of stem is 1.5 to 2 centimeter long. The stem pieces are further dried in shade and are fed into the pulveriser with a 5 millimeter mesh size and further a 3 millimeter mesh size to yield a homogenous powder of average particle size of 1 millimeter to 3 millimeters.

p) Fruits with seeds and stem bark of *Zizyphus jujuba* Lamk.: Fresh fruits of *Zizyphus jujuba* Lamk are collected and cleaned well with water to remove any impurities. The fruits are then wiped dry and dried in direct sun-light. The dried fruits are then powdered in pulverizers of mesh size between 5 millimeters and then and 3 millimeters, to get a homogenous powder of average particle size of 1 millimeter to 3 millimeters. The stem bark of *Zizyphus jujuba* Lamk are sheared off so as not to remove the entire cross section of the bark which might cause the plant to whither. The sheared bark are cleaned with water and dried in indirect sunlight. Further it is cut into pieces of 1.5 centimeter to 2 centimeter and further dried in shade. The dried pieces of stem bark and then fed into pulverizers of mesh size 3 millimeters, to get a homogenous powder of average particle size of 1 millimeter to 3 millimeters.

While using the respective substitutes to the preferred herbal ingredients, the corresponding parts of the substitute plants may be used and prepared in exactly the same way as the original ingredients except in three cases, which are as explained below:

i. When *Centella asiatica* (L) Urban is being substituted with *Strychnos nuxvomica* L: Leaves of *Strychnos nuxvomica* L is the most preferred part to be used for substitution. Fresh leaves of *Strychnos nuxvomica* L are collected, washed in water to remove physical impurities. The leaves are cut into pieces of 1.5 centimeters to 2 centimeters and then dried under shade. The dried leaves are then pulverized using 3 millimeter mesh size to yield a homogenous powder of average particle size of 1 millimeter to 3 millimeters.

ii. Further, when *Centella asiatica* (L) Urban is being substituted with *Butea frondosa* Koen. Ex Roxb: Flowers of *Butea frondosa* Koen. Ex Roxb are the most preferred part to be used for substitution. Fresh flowers of *Butea frondosa* Koen. Ex Roxb are collected, washed in water to remove physical impurities. The flowers are cut into pieces of 1.5 centimeters to 2 centimeters and then dried under shade. The dried flowers are then pulverized using 3 millimeter mesh size to yield a homogenous powder of average particle size of 1 millimeter to 3 millimeters.

iii. And again when *Centella asiatica* (L) Urban is being substituted with *Acacia catechu* (L.f) Willd: Heart wood of *Acacia catechu* (L.f) Willd is the most preferred part to be used for substitution. Heart wood of *Acacia catechu* (L.f) Willd are collected, washed in water to remove physical impurities. The heart wood are then cut into pieces of 1.5 centimeters to 2 centimeters and then dried under direct sunlight. The dried wood is fed into the pulveriser with a 5 millimeter mesh size and further a 3 millimeter mesh size to yield a homogenous powder of average particle size of 1 millimeter to 3 millimeters.

An embodiment of the present invention for prevention and treatment of the diabetes and associated complications comprises:

a) Fruits without seeds of the Species *Emblica officinalis* Gaertn. (Synonym: *Phyllanthus emblica* L.) of the Euphorbiaceae Family, 5 to 8% by w/w;
b) Roots of Species of herbs of the Genus *Salacia* of the of the Celastraceae family, 10 to 15% by w/w;
c) Seeds of the Species *Strychnos potatorum* L. f. of the Strychnaceae family, 5 to 8% by w/w;
d) Roots of the Species *Vetiveria zizanioides* (L.) Nash (Synonym: *Andropogon squarrosus* Hook f. (non L. f.) of the Poaceae family, 1 to 5% by w/w;
e) Rhizomes of the Species *Curcuma longa* L. of the Zingiberaceae family, 5 to 8% by w/w;
f) Whole plant of Species of herbs of the Genus *Aerva* of the Amaranthaceae family, 5 to 8% by w/w;
g) Whole plant of Species of herbs of the Genus *Biophytum* of the Oxalidaceae family, 1 to 5% by w/w;
h) Seeds of Species of herbs of the Genus *Syzygium* of the Myrtaceae family, 5 to 8% by w/w;
i) Seeds kernels of the Species *Mangifera indica* L. of the Anacardiaceae family, 1 to 5% by w/w;

j) Tuberous roots of Species of herbs of the Genus *Cyclea* and/or roots of the Genus *Cissampelos* of the Menispermaceae family, 1 to 5% by w/w;
k) Seeds of Species of herbs of the Genus *Embelia* of the Myrsinaceae family, 1 to 5% by w/w;
l) Rhizomes of Species of herbs of the Genus *Cyperus* of the Cyperaceae family, 1 to 5% by w/w;
m) Fruits without seeds of the Species *Terminalia chebula* (Gaertn.) Retz. of the Combretaceae family, 15 to 30% by w/w;
n) Whole plant of the Species *Centella asiatica* (L.) Urban of the Apiaceae family and/or leaves of the Species *Strychnos nux-vomica* L. (Synonym: *Strychnos ligustrina* Blume) of the Strychnaceae family, and/or flowers of the Species *Butea frondosa* Koen. ex Roxb. (synonym: *Butea monosperma* (Lam.) Taub. of the Papilionaceae family and/or heart wood of the Species *Acacia catechu* (L.f.) Willd. of the Mimosaceae family, 1 to 5% by w/w;
o) Stem with bark of the Species *Coscinium fenestratum* (Gaertn.) Colebr. of the Menispermaceae family and/or stem with bark of Species of herbs of the Genus *Berberis* of the Berberidaceae family, 5 to 8% w/w and
p) Fruits with seeds and stem bark of Species of herbs of the Genus *Zizyphus* of the Rhamnaceae family, 1 to 5% by w/w, Wherein the ingredients are powdered to 1 millimeter to 3 millimeter particle size and blended in a blender at 30 to 60 rotations per minutes to obtain the homogenous herbal formulation.

A preferred embodiment of the present invention for prevention and treatment of the diabetes and associated complications comprises:
a) Fruits without seeds of *Emblica officinalis* Gaertn. (Synonym: *Phyllanthus emblica* L.) of the Euphorbiaceae Family, 5 to 8% by w/w
b) Roots of *Salacia oblonga* Wall. ex Wight & Arn. of the of the Celastraceae family, 10 to 15% by w/w
c) Seeds of *Strychnos potatorum* L. f. of the Strychnaceae family, 5 to 8% by w/w;
d) Roots of *Vetiveria zizanioides* (L.) Nash (Synonym: *Andropogon squarrosus* Hook f. (non L. f.) of the Poaceae family, 1 to 5% by w/w
e) Rhizomes of *Curcuma longa* L. of the Zingiberaceae family, 5 to 8% by w/w
f) Whole plant of *Aerva lanata* Juss of the Amaranthaceae family, 5 to 8% by w/w
g) Whole plant of *Biophytum sensitivum* (L.) DC. (Synonym: *Oxalis sensitivum* L.) of the Oxalidaceae family, 1 to 5% by w/w
h) Seeds of *Syzygium cumini* (L.) Skeels (Synonym: *Eugenia jambolana* Lam.) of the Myrtaceae family, 5 to 8% by w/w;
i) Seeds kernels of *Mangifera indica* L. of the Anacardiaceae family, 1 to 5% by w/w;
j) Tuberous roots of *Cyclea peltata* (Lam.) Hook. f. & Thorns. of the Menispermaceae family, 1 to 5% by w/w;
k) Seeds of *Embelia ribes* Burm. f. of the Myrsinaceae family, 1 to 5% by w/w
l) Rhizomes of *Cyperus rotundus* L., (Synonym: *Cyperus rotundus* L. ssp. *tuberosus* (Rottb.) Kuekenth; and *Cyperus tuberosus* Rottb.) of the Cyperaceae family, 1 to 5% by w/w
m) Fruits without seeds of *Terminalia chebula* (Gaertn.) Retz. of the Combretaceae family, 15 to 30% by w/w
n) Whole plant of *Centella asiatica* (L.) Urban of the Apiaceae family, 1 to 5% by w/w
o) Stem with bark of *Coscinium fenestratum* (Gaertn.) Colebr. of the Menispermaceae family, 5 to 8% w/w, and
p) Fruits with seeds and stem bark of *Zizyphus jujuba* Lamk. (Synonym: *Zizyphus mauritiana* Lamk.) of the Rhamnaceae family, 1 to 5% by w/w Wherein the ingredients are powdered to 1 millimeter to 3 millimeter particle size and blended in a blender at 30 to 60 rotations per minutes to obtain the homogenous herbal formulation.

The above mentioned formulation reduces levels of blood sugar as evidenced by before and after Fasting and Postprandial Blood readings and also reduces the glycosylation of hemoglobin as evidenced by before and after HB1AC values. The above formulation also reduces Total cholesterol, LDL Cholesterol and Serum Triglycrides in before and after trials and at the same time it increases the HDL cholesterol. The above formulation additionally offers improved cardiovascular health for diabetics simultaneously suffering from cardio vascular diseases as evidenced by reduction of hypertension and improved exercise tolerance. It also reduces serum creatinine and also improves the quality of life of the diabetic as evidenced by reduction in pain and numbness, improved sleep and improved bowel evacuation. The above formulation also offers the additional benefit of improved wound healing for diabetics. Thus the use of the above composition improves the chances of wound healing as evidenced by reduced time in complete healing of diabetic ulcers. The above formulation also offers the benefit of improved ocular health for diabetics as evidenced by reduction in the incidence of diabetes related retinal capillary bleedings and slowing down in the progress of diabetic retinopathy and cataract. It also offers the additional benefit of better dermal health for diabetics and management of skin ailments of diabetics as evidenced by faster resolving of boils, carbuncles etc which occur very often in diabetics. Further it offers better quality of sleep as evidenced by improvement in sleep patterns of diabetics previously recorded as having disturbed sleep. Furthermore the formulation has the additional benefit of reducing the size of the prostrate gland in male diabetics suffering from benign prostratic hypertrophy. This formulation also offers an equally good or significantly better option of control for people with identified pre-diabetic conditions and newly identified diabetics when compared with diet and exercise alone or also as an adjuvant to diet and exercise. The composition also acts as an excellent adjuvant with other hypoglycemic drugs and helps to reduce their dose.

An embodiment of the present invention for prevention and treatment of the diabetes comprises:
a) Fruits without seeds of the Species *Emblica officinalis* Gaertn. (Synonym: *Phyllanthus emblica* L.) of the Euphorbiaceae Family, 15 to 30% by w/w;
b) Roots of Species of herbs of the Genus *Salacia* of the of the Celastraceae family, 10 to 30% by w/w;
c) Rhizomes of the Species *Curcuma longa* L. of the Zingiberaceae family, 15 to 30%, w/w;
d) Seeds of Species of herbs of the Genus *Syzygium* of the Myrtaceae family, 10 to 30% by w/w;
e) Seeds kernels of the Species *Mangifera indica* L. of the Anacardiaceae family, 5 to 25% by w/w and
f) Tuberous roots of Species of herbs of the Genus *Cyclea* and/or roots of the Genus *Cissampelos* of the Menispermaceae family, 5 to 25% by w/w Wherein the ingredients are powdered to 1 millimeter to 3 millimeter particle size and blended in a blender at 30 to 60 rotations per minutes to obtain the homogenous herbal formulation.

A preferred embodiment of the present invention for prevention and treatment of the diabetes comprises:
- a) Fruits without seeds of *Emblica officinalis* Gaertn. (Synonym: *Phyllanthus emblica* L.) of the Euphorbiaceae Family, 15 to 30% by w/w,
- b) Roots of *Salacia oblonga* Wall. ex Wight & Arn. of the of the Celastraceae family, 10 to 30% by w/w,
- c) Rhizomes of *Curcuma longa* L. of the Zingiberaceae family, 15 to 30%, w/w,
- d) Seeds of *Syzygium cumini* (L.) Skeels (Synonym: *Eugenia jambolana* Lam.) of the Myrtaceae family, 10 to 30% by w/w,
- e) Seeds kernels of *Mangifera indica* L. of the Anacardiaceae family, 5 to 25% by w/w and
- f) Tuberous roots of *Cyclea peltata* (Lam.) Hook. f. & Thorns. of the Menispermaceae family, 5 to 25% by w/w.

Wherein the ingredients are powdered to 1 millimeter to 3 millimeter particle size and blended in a blender at 30 to 60 rotations per minutes to obtain the homogenous herbal formulation.

The above mentioned formulation reduces levels of blood sugar as evidenced by before and after Fasting and Postprandial Blood readings and also reduces the glycosylation of hemoglobin as evidenced by before and after HbA1C values. This formulation also offers an equally good or significantly better option of control for people with identified pre-diabetic conditions and newly identified diabetics when compared with diet and exercise alone or also as an adjuvant to diet and exercise. The composition also acts as an excellent adjuvant with other hypoglycemic drugs and helps to reduce their dose.

An embodiment of the present invention for prevention and treatment of renal complications associated with diabetes comprises:
- a) Seeds of the Species *Strychnos potatorum* L. f. of the Strychnaceae family, 20 to 30% by w/w;
- b) Roots of the Species *Vetiveria zizanioides* (L.) Nash (Synonym: *Andropogon squarrosus* Hook f. (non L. f.) of the Poaceae family, 10 to 30% by w/w;
- c) Whole plant of Species of herbs of the Genus *Aerva* of the Amaranthaceae family, 20 to 40% by W/w;
- d) Tuberous roots of Species of herbs of the Genus *Cyclea* and/or roots of the Genus *Cissampelos* of the Menispermaceae family, 5 to 20% by w/w and
- e) Rhizomes of Species of herbs of the Genus *Cyperus* of the Cyperaceae family, 5 to 20% by w/w Wherein the ingredients are powdered to 1 millimeter to 3 millimeter particle size and blended in a blender at 30 to 60 rotations per minutes to obtain the homogenous herbal formulation.

A preferred embodiment of the present invention for prevention and treatment of renal complications associated with diabetes comprises:
- a) Seeds of *Strychnos potatorum* L. f. of the Strychnaceae family, 20 to 30% by w/w,
- b) Roots of *Vetiveria zizanioides* (L.) Nash (Synonym: *Andropogon squarrosus* Hook f. (non L. f.) of the Poaceae family, 10 to 30% by w/w,
- c) Whole plant of *Aerva lanata* Juss of the Amaranthaceae family, 20 to 40% by w/w,
- d) Tuberous roots of *Cyclea peltata* (Lam.) Hook. f. & Thorns. of the Menispermaceae family, 5 to 20% by w/w, and
- e) Rhizomes of *Cyperus rotundus* L., (Synonym: *Cyperus rotundus* L. ssp. *tuberosus* (Rottb.) Kuekenth; and *Cyperus tuberosus* Rottb.) of the Cyperaceae family, 5 to 20% by w/w.

Wherein the ingredients are powdered to 1 millimeter to 3 millimeter particle size and blended in a blender at 30 to 60 rotations per minutes to obtain the homogenous herbal formulation.

The above mentioned formulation improves the renal health and reduces levels of serum creatinine. The main advantage of the invention is that it provides a safe and effective herbal formulation which can improve the renal health and thereby also reduce the elevated levels of serum creatinine.

An embodiment of the present invention for prevention and treatment of retinopathy associated with diabetes comprises:
- a) Fruits without seeds of the Species *Emblica officinalis* Gaertn. (Synonym: *Phyllanthus emblica* L.) of the Euphorbiaceae Family, 20 to 30% by w/w;
- b) Seeds of the Species *Strychnos potatorum* L. f. of the Strychnaceae family, 20 to 30% by w/w;
- c) Rhizomes of the Species *Curcuma longa* L. of the Zingiberaceae family, 20 to 30%, w/w and
- d) Stem with bark of the Species *Coscinium fenestratum* (Gaertn.) Colebr. of the Menispermaceae family and/or stem with bark of Species of herbs of the Genus *Berberis* of the Berberidaceae family, 20 to 30% w/w Wherein the ingredients are powdered to 1 millimeter to 3 millimeter particle size and blended in a blender at 30 to 60 rotations per minutes to obtain the homogenous herbal formulation.

A preferred embodiment of the present invention for prevention and treatment of retinopathy associated with diabetes comprises:
- a) Fruits without seeds of *Emblica officinalis* Gaertn. (Synonym: *Phyllanthus emblica* L.) of the Euphorbiaceae Family, 20 to 30% by w/w,
- b) Seeds of *Strychnos potatorum* L. f. of the Strychnaceae family, 20 to 30% by w/w,
- c) Rhizomes of *Curcuma longa* L. of the Zingiberaceae family, 20 to 30% by w/w, and
- d) Stem with bark of *Coscinium fenestratum* (Gaertn.) Colebr. of the Menispermaceae family, 20 to 30% by w/w.

Wherein the ingredients are powdered to 1 millimeter to 3 millimeter particle size and blended in a blender at 30 to 60 rotations per minutes to obtain the homogenous herbal formulation.

The main advantage of the above invention is that it provides safe and effective herbal formulation which prevents, manages and treats diabetic retinopathy and offers arrest to the progress of the disease.

An embodiment of the present invention for prevention and treatment of oxidative damage to heart and its blood vessels associated with diabetes comprises:
- a) Roots of Species of herbs of the Genus *Salacia* of the of the Celastraceae family, 10 to 30% by w/w;
- b) Seeds kernels of the Species *Mangifera indica* L. of the Anacardiaceae family, 10 to 20% by w/w;
- c) Rhizomes of Species of herbs of the Genus *Cyperus* of the Cyperaceae family, 10 to 20% by w/w;
- d) Fruits without seeds of the Species *Terminalia chebula* (Gaertn.) Retz. of the Combretaceae family, 20 to 50% by w/w and
- e) Fruits with seeds and stem bark of Species of herbs of the Genus Zizyphus of the Rhamnaceae family, 10 to 20% by w/w, Wherein the ingredients are powdered to 1 millimeter to 3 millimeter particle size and blended in a blender at 30 to 60 rotations per minutes to obtain the homogenous herbal formulation.

A preferred embodiment of the present invention for prevention and treatment of oxidative damage to heart and its blood vessels, associated with diabetes) comprises:

a) *Salacia oblonga* Wall. ex Wight & Arn. of the of the Celastraceae family, 10 to 30% by w/w,
b) *Mangifera indica* L. of the Anacardiaceae family, 10 to 20% by w/w,
c) *Cyperus rotundus* L., (Synonym: *Cyperus rotundus* L. ssp. *tuberosus* (Rottb.) Kuekenth; and *Cyperus tuberosus* Rottb.) of the Cyperaceae family, 10 to 20% by w/w,
d) *Terminalia chebula* (Gaertn.) Retz. of the Combretaceae family, 20 to 50% by w/w, and
e) *Zizyphus jujuba* Lamk. (Synonym: *Zizyphus mauritiana* Lamk.) of the Rhamnaceae family, 10 to 20% by w/w.

Wherein the ingredients are powdered to 1 millimeter to 3 millimeter particle size and blended in a blender at 30 to 60 rotations per minutes to obtain the homogenous herbal formulation.

The main advantage of the above invention is that it provides safe and effective herbal formulation which simultaneously prevents oxidative damage to heart and its blood vessels and also reduces hypertension. According to another embodiment of the present invention, the formulations described in any of the preceeding embodiments are processed as an extract/concentrate.

Still in another embodiment of the present invention, the formulations described in any of the preceeding embodiments are processed as an extract/concentrate and further formulated using known conventional processes in the form of capsules or tablets or syrups or eye drops or dermal patches or nasal sprays or injectable medicine or ointments or gels absorbable through skin.

In yet another embodiment of the present invention, the formulations described in any of the preceeding embodiments is processed as extract/concentrate and is further formulated using known conventional processes to appropriate pharmacological formulations, suitable digestive, flavoring, exciepient and/or absorptive pharmacological adjuvants, which are normally used in such formulations, as per the specific requirements are added.

Thus the composition of the present invention is not a mere mixture of the ingredients used resulting in aggregation of their properties but a mixture having synergistically enhanced properties useful in prevention of oxidative damage to heart and its blood vessels and which reduces hypertension.

The inventions are described with reference to the examples, which are provided by way of illustration only, and these examples should not be construed to limit the scope of the present invention:

Examples of Process for Preparation of Herbal Formulation for Prevention and Treatment of the Diabetes and Associated Complications Example 1

As per this Example, one kilogram of the formulation is made by using Fruits without seeds of *Emblica officinalis* Gaertn. (Synonym: *Phyllanthus emblica* L.) of the Euphorbiaceae Family, 80 grams, Roots of *Salacia oblonga* Wall. ex Wight & Arn. of the of the Celastraceae family, 100 grams, Seeds of *Strychnos potatorum* L. f. of the Strychnaceae family, 80 grams; Roots of *Vetiveria zizanioides* (L.) Nash (Synonym: *Andropogon squarrosus* Hook f. (non L. f.) of the Poaceae family, 50 grams, Rhizomes of *Curcuma longa* L. of the Zingiberaceae family, 80 grams, Whole plant of *Aerva lanata* Juss of the Amaranthaceae family, 80 grams, Whole plant of *Biophytum sensitivum* (L.) DC. (Synonym: *Oxalis sensitivum* L.) of the Oxalidaceae family, 50 grams, Seeds of *Syzygium cumini* (L.) Skeels (Synonym: *Eugenia jambolana* Lam.) of the Myrtaceae family, 80 grams; Seeds kernels of *Mangifera indica* L. of the Anacardiaceae family, 50 grams, Tuberous roots of *Cyclea peltata* (Lam.) Hook. f. & Thorns. of the Menispermaceae family, 50 grams; Seeds of *Embelia ribes* Burm. f. of the Myrsinaceae family, 15 grams, Rhizomes of *Cyperus rotundus* L., (Synonym: *Cyperus rotundus* L. ssp. *tuberosus* (Rottb.) Kuekenth; and *Cyperus tuberosus* Rottb.) of the Cyperaceae family, 50 grams, Fruits without seeds of *Terminalia chebula* (Gaertn.) Retz. of the Combretaceae family, 150 grams, Whole plant of *Centella asiatica* (L.) Urban of the Apiaceae family, 10 grams, Stem with bark of *Coscinium fenestratum* (Gaertn.) Colebr. of the Menispermaceae family, 50 grams, and Fruits with seeds of *Zizyphus jujuba* Lamk. (Synonym: *Zizyphus mauritiana* Lamk.) of the Rhamnaceae family, 25 grams.

The herbs are taken in the above proportion and powdered. The powders are mixed to get the composition of the Example 1. The composition prepared as described above is dispensed as sachets containing 6 grams in it. The content of the sachet is to be added to one and half to two liters of water in a suitable vessel and boiled for two minutes. Then the powdered composition is to be strained and removed from the vessel to be dispensed off. The water so made is to be completely used up by the diabetic patient in twenty four hours, using it instead of drinking water, in 8 or 6 divided doses.

Example 2

As per this Example, one kilogram of the formulation is made by using Fruits without seeds of *Emblica officinalis* Gaertn. (Synonym: *Phyllanthus emblica* L.) of the Euphorbiaceae Family, 100 grams, Roots of *Salacia oblonga* Wall. ex Wight & Arn. of the of the Celastraceae family, 100 grams, Seeds of *Strychnos potatorum* L. f. of the Strychnaceae family, 80 grams; Roots of *Vetiveria zizanioides* (L.) Nash (Synonym: *Andropogon squarrosus* Hook f. (non L. f.) of the Poaceae family, 40 grams, Rhizomes of *Curcuma longa* L. of the Zingiberaceae family, 80 grams, Whole plant of *Aerva lanata* Juss of the Amaranthaceae family, 80 grams, Whole plant of *Biophytum sensitivum* (L.) DC. (Synonym: *Oxalis sensitivum* L.) of the Oxalidaceae family, 40 grams, Seeds of *Syzygium cumini* (L.) Skeels (Synonym: *Eugenia jambolana* Lam.) of the Myrtaceae family, 80 grams; Seeds kernels of *Mangifera indica* L. of the Anacardiaceae family, 50 grams, Tuberous roots of *Cyclea peltata* (Lam.) Hook. f. & Thorns. of the Menispermaceae family, 50 grams; Seeds of *Embelia ribes* Burm. f. of the Myrsinaceae family, 15 grams, Rhizomes of *Cyperus rotundus* L., (Synonym: *Cyperus rotundus* L. ssp. *tuberosus* (Rottb.) Kuekenth; and *Cyperus tuberosus* Rottb.) of the Cyperaceae family, 50 grams, Fruits without seeds of *Terminalia chebula* (Gaertn.) Retz. of the Combretaceae family, 150 grams, Whole plant of *Centella asiatica* (L.) Urban of the Apiaceae family, 10 grams, Stem with bark of *Coscinium fenestratum* (Gaertn.) Colebr. of the Menispermaceae family, 50 grams, and Fruits with seeds of *Zizyphus jujuba* Lamk. (Synonym: *Zizyphus mauritiana* Lamk.) of the Rhamnaceae family, 25 grams.

The specified parts of the above mentioned herbs were taken in the above mentioned proportion and powdered. The powders were mixed to get the formulation. The formulation prepared as described above is dispensed as sachets containing 6 grams in each sachet. When used the content of the sachet is to be added to one and half to two liters of water in a suitable vessel and boiled for two minutes. Then the powdered composition is to be strained and removed from the vessel to be dispensed off. The water so made is to be completely used up by the diabetic patient in twenty four hours, in 8 or 6 divided doses.

Example 3

As per this Example, one kilogram of the formulation is made by using Fruits without seeds of *Emblica officinalis* Gaertn. (Synonym: *Phyllanthus emblica* L.) of the Euphorbiaceae Family, 80 grams, Roots of *Salacia oblonga* Wall. ex Wight & Arn. of the of the Celastraceae family, 100 grams, Seeds of *Strychnos potatorum* L. f. of the Strychnaceae family, 80 grams; Roots of *Vetiveria zizanioides* (L.) Nash (Synonym: *Andropogon squarrosus* Hook f. (non L. f.) of the Poaceae family, 40 grams, Rhizomes of *Curcuma longa* L. of the Zingiberaceae family, 80 grams, Whole plant of *Aerva lanata* Juss of the Amaranthaceae family, 80 grams, Whole plant of *Biophytum sensitivum* (L.) DC. (Synonym: *Oxalis sensitivum* L.) of the Oxalidaceae family, 40 grams, Seeds of *Syzygium cumini* (L.) Skeels (Synonym: *Eugenia jambolana* Lam.) of the Myrtaceae family, 80 grams; Seeds kernels of *Mangifera indica* L. of the Anacardiaceae family, 50 grams, Tuberous roots of *Cyclea peltata* (Lam.) Hook. f. & Thorns. of the Menispermaceae family, 50 grams; Seeds of *Embelia ribes* Burm. f. of the Myrsinaceae family, 15 grams, Rhizomes of *Cyperus rotundus* L., (Synonym: *Cyperus rotundus* L. ssp. *tuberosus* (Rottb.) Kuekenth; and *Cyperus tuberosus* Rottb.) of the Cyperaceae family, 50 grams, Fruits without seeds of *Terminalia chebula* (Gaertn.) Retz. of the Combretaceae family, 170 grams, Whole plant of *Centella asiatica* (L.) Urban of the Apiaceae family, 10 grams, Stem with bark of *Coscinium fenestratum* (Gaertn.) Colebr. of the Menispermaceae family, 50 grams, and Fruits with seeds of *Zizyphus jujuba* Lamk. (Synonym: *Zizyphus mauritiana* Lamk.) of the Rhamnaceae family, 25 grams.

The herbs are taken in the above proportion mixed and made into coarse powder using a pulveriser. The powder so made is extracted using water as a solvent. Water from the resultant extract is completely evaporated to get dried flakes of the extract which is then again powdered to get fine powder of the composition which makes up the active ingredient part of the formulation of the invention described in this Example 3.

This active ingredient powder of the formulation constitutes 0.625 grams of the 1 gram tablets. The rest of the 0.375 grams of each of the 1 gram tablet is constituted by binders and exciepients of which some are digestive, flavoring and absorptive adjuvants. The composition of the exciepients and binders in a 1 gram tablet is 0.022 grams of *Ipomoea batatas*, 0.017 grams of *Elettaria cardamom*, 0.023 grams of *Piper longum*, 0.0145 grams of *Cuminum ciminum* 0.016 grams of Di-calcium Phosphate IP, 0.015 grams of PVPK-30, 0.0004 grams each of Methyl paraben IP, Propyl paraben IP and colloidal silicon dioxide-IP, 0.0003 grams of talcum powder, 0.001 gram of Magnesium Stearate, 0.06 grams of Microcrystalline cellulose powder, 0.2 grams of IPA-IP and 0.005 grams of Aspartame, together constituting 0.375 grams. Tablets are made using these ingredients in the above said ratio and in the conventional methods of tablet making.

The above embodiment of the formulation as a tablet is orally administered to the diabetic patients as one tablet, four times a day. The tablet is to be sublingually placed to dissolve over ten minutes before food or to be chewed and swallowed by the patient within ten minutes after food.

Examples of the process of the preparation of herbal formulation used for the prevention and treatment of diabetes:

Example 4

As per this Example, 100 grams of the formulation is made by using 20 grams each of Dried fruits of *Emblica officinalis*, Dried roots of *Salacia oblonga*, Dried rhizomes of *Curcuma longa*, dried leaves or seeds or seeds kernels of *Mangifera indica* and 10 grams each of dried tuberous roots of *Cyclea peltata* and Seeds of *Sizygium cumini*.

The herbs are taken in the above proportion and powdered. The powders are mixed to get the composition of the Example 1. The composition prepared as described above is dispensed as sachets containing 6 grams in it. The content of the sachet is to be added to one and half to two liters of water in a suitable vessel and boiled for two minutes. Then the powdered composition is to be strained and removed from the vessel to be dispensed off. The water so made is to be completely used up by the diabetic patient in twenty four hours, using it instead of drinking water, in 8 or 6 divided doses.

Example 5

As per this example; 100 grams of the formulation is made using 25 grams each of Dried fruits of *Emblica officinalis*, Dried roots of *Salacia oblonga*, Dried rhizomes of *Curcuma longa*, and 15 grams of Seeds of *Sizygium cumini* and 5 grams each of Dried leaves or seeds or seeds kernels of *Mangifera indica*, Dried tuberous roots of *Cyclea peltata*.

The specified parts of the above mentioned herbs were taken in the above mentioned proportion and powdered. The powders were mixed to get the formulation. The formulation prepared as described above is dispensed as sachets containing 6 grams in each sachet. When used the content of the sachet is to be added to one and half to two liters of water in a suitable vessel and boiled for two minutes. Then the powdered composition is to be strained and removed from the vessel to be dispensed off. The water so made is to be completely used up by the diabetic patient in twenty four hours, in 8 or 6 divided doses.

Example 6

In this Example 6 of the invention, 100 grams of the composition is made using 30 grams each, Dried rhizomes of *Curcuma longa*, and Dried fruits of *Emblica officinalis* and 10 grams each of Dried roots of *Salacia oblonga*, Seeds of *Sizygium cumini*, and Dried tuberous roots of *Cyclea peltata*, and Dried seeds kernels of *Mangifera indica*.

The herbs are taken in the above proportion mixed and made into coarse powder using a pulveriser. The powder so made is extracted using water as a solvent. Water from the resultant extract is completely evaporated to get dried flakes of the extract which is then again powdered to get fine powder of the composition which makes up the active ingredient part of the formulation of the invention described in this Example 6.

This active ingredient powder of the formulation constitutes 0.625 grams of the 1 gram tablets. The rest of the 0.375 grams of each of the 1 gram tablet is constituted by binders and exciepients of which some are digestive, flavoring and absorptive adjuvants. The composition of the exciepients and binders in a 1 gram tablet is 0.022 grams of *Ipomoea batatas*, 0.017 grams of *Elettaria cardamom*, 0.023 grams of *Piper longum*, 0.0145 grams of *Cuminum ciminum* 0.016 grams of Di-calcium Phosphate IP, 0.015 grams of PVPK-30, 0.0004 grams each of Methyl paraben IP, Propyl paraben IP and colloidal silicon dioxide-IP, 0.0003 grams of talcum powder, 0.001 gram of Magnesium Stearate, 0.06 grams of Microcrystalline cellulose powder, 0.2 grams of IPA-IP and 0.005 grams of Aspartame, together constituting 0.375 grams. Tablets are made using these ingredients in the above said ratio and in the conventional methods of tablet making.

The above embodiment of the formulation as a tablet is orally administered to the diabetic patients as one tablet, four times a day. The tablet is to be sublingually placed to dissolve over ten minutes before food or to be chewed and swallowed by the patient within ten minutes after food.

Examples of Process for Preparation of Herbal Formulation for Prevention and Treatment of Renal Complications Associated with Diabetes Example 7

As per this Example, 100 grams of the formulation is made by using 20 grams each of Dried Seeds of *Strychnos potatorum*, Dried roots of *Vetiveria zizaniodes*, dried whole plant of *Aerva lanata*, dried tuberous roots of *Cyclea peltata* and Dried rhizomes of *Cyperus rotundus*.

The herbs are taken in the above proportion and powdered. The powders are mixed to get the composition of the Example 1. The composition prepared as described above is dispensed as sachets containing 6 grams in it. The content of the sachet is to be added to one and half to two liters of water in a suitable vessel and boiled for two minutes. Then the powdered composition is to be strained and removed from the vessel to be dispensed off. The water so made is to be completely used up by the diabetic patient in twenty four hours, using it instead of drinking water, in 8 or 6 divided doses.

Example 8

As per this example; 100 grams of the formulation is made using 30 grams each Dried roots of *Vetiveria zizaniodes*, Seeds of *Strychnos potatorum* and Dried whole plant of *Aerva lanata* and 5 grams each of Dried rhizomes of *Cyperus rotundus* and Dried tuberous roots of *Cyclea peltata*.

The specified parts of the above mentioned herbs were taken in the above mentioned proportion and powdered. The powders were mixed to get the formulation. The formulation prepared as described above is dispensed as sachets containing 25 grams in each sachet. When used the content of the sachet is to be added to one and half to two liters of water in a suitable vessel and boiled for two minutes. Then the powdered composition is to be strained and removed from the vessel to be dispensed off. The water so made is to be completely used up by the diabetic patient in twenty four hours, in 8 or 6 divided doses.

Example 9

In this Example 9 of the invention, 100 grams of the composition is made using 40 grams of Dried whole plant of *Aerva lanata* and 30 grams of Seeds of *Strychnos potatorum* and 10 grams each of Dried rhizomes of *Cyperus rotundus*, Dried roots of *Vetiveria zizaniodes* and Dried tuberous roots of *Cyclea peltata*.

The herbs are taken in the above proportion mixed and made into coarse powder using a pulveriser. The powder so made is extracted using water as a solvent. Water from the resultant extract is completely evaporated to get dried flakes of the extract which is then again powdered to get fine powder of the composition which makes up the active ingredient part of the formulation of the invention described in this Example 9.

This active ingredient powder of the formulation constitutes 0.625 grams of the 1 gram tablets. The rest of the 0.375 grams of each of the 1 gram tablet is constituted by binders and excieipients of which some are digestive, flavoring and absorptive adjuvants. The composition of the excieipients and binders in a 1 gram tablet is 0.022 grams of *Ipomoea batatas*, 0.017 grams of *Elettaria cardamom*, 0.023 grams of *Piper longum*, 0.0145 grams of *Cuminum ciminum* 0.016 grams of Di-calcium Phosphate IP, 0.015 grams of PVPK-30, 0.0004 grams each of Methyl paraben IP, Propyl paraben IP and colloidal silicon dioxide-IP, 0.0003 grams of talcum powder, 0.001 gram of Magnesium Stearate, 0.06 grams of Microcrystalline cellulose powder, 0.2 grams of IPA-IP and 0.005 grams of Aspartame, together constituting 0.375 grams. Tablets are made using these ingredients in the above said ratio and in the conventional methods of tablet making.

The above embodiment of the formulation as a tablet is orally administered to the diabetic patients as one tablet, four times a day. The tablet is to be sublingually placed to dissolve over ten minutes before food or to be chewed and swallowed by the patient within ten minutes after food.

Examples of Process for Preparation of the Herbal Formulation Used for the Prevention and Treatment of Retinopathy Associated with Diabetes Example 10

As per this Example, 100 grams of the formulation is made by using 25 grams each of Dried fruits of *Emblica officinalis*, Seeds of *Strychnos potatorum*, Dried rhizomes of *Curcuma longa*, and dried Stem with bark of *Coscinium fenestratum*.

The herbs are taken in the above proportion and powdered. The powders are mixed to get the composition of the Example 1. The composition prepared as described above is dispensed as sachets containing 8 grams in it. The content of the sachet is to be added to one and half to two liters of water in a suitable vessel and boiled for two minutes. Then the powdered composition is to be strained and removed from the vessel to be dispensed off. The water so made is to be completely used up by the diabetic patient in twenty four hours, using it instead of drinking water, in 8 or 6 divided doses.

Example 11

As per this example, 100 grams of the formulation is made using 30 grams each of Dried fruits of *Emblica officinalis* and Dried rhizomes of *Curcuma longa* and 20 grams each of Seeds of *Strychnos potatorum* and dried Stem with bark of *Coscinium fenestratum*.

The specified parts of the above mentioned herbs were taken in the above mentioned proportion and powdered. The powders were mixed to get the formulation. The formulation prepared as described above is dispensed as sachets containing 10 grams in each sachet. When used the content of the sachet is to be added to one and half to two liters of water in a suitable vessel and boiled for two minutes. Then the powdered composition is to be strained and removed from the vessel to be dispensed off. The water so made is to be completely used up by the diabetic patient in twenty four hours, in 8 or 6 divided doses.

Example 12

In this Example 12 of the invention, 100 grams of the composition is made using 20 grams each of Dried fruits of

*Emblica officinalis* and Dried rhizomes of *Curcuma longa* and 30 grams each of Seeds of *Strychnos potatorum* and dried Stem with bark of *Coscinium fenestratum*.

The herbs are taken in the above proportion mixed and made into coarse powder using a pulveriser. The powder so made is extracted using water as a solvent. Water from the resultant extract is completely evaporated to get dried flakes of the extract which is then again powdered to get fine powder of the composition which makes up the active ingredient part of the formulation of the invention described in this Example 12.

This active ingredient powder of the formulation constitutes 0.625 grams of the 1 gram tablets. The rest of the 0.375 grams of each of the 1 gram tablet is constituted by binders and exciepients of which some are digestive, flavoring and absorptive adjuvants. The composition of the exciepients and binders in a 1 gram tablet is 0.022 grams of *Ipomoea batatas*, 0.017 grams of *Elettaria cardamom*, 0.023 grams of *Piper longum*, 0.0145 grams of *Cuminum ciminum* 0.016 grams of Di-calcium Phosphate IP, 0.015 grams of PVPK-30, 0.0004 grams each of Methyl paraben IP, Propyl paraben IP and colloidal silicon dioxide-IP, 0.0003 grams of talcum powder, 0.001 gram of Magnesium Stearate, 0.06 grams of Microcrystalline cellulose powder, 0.2 grams of IPA-IP and 0.005 grams of Aspartame, together constituting 0.375 grams. Tablets are made using these ingredients in the above said ratio and in the conventional methods of tablet making.

The above embodiment of the formulation as a tablet is orally administered to the diabetic patients as one tablet, four times a day. The tablet is to be sublingually placed to dissolve over ten minutes before food or to be chewed and swallowed by the patient within ten minutes after food.

Examples for the Process of Preparation for Herbal Formulation for Prevention and Treatment of Oxidative Damage to Heart and its Blood Vessels Associated with Diabetes Example 13

As per this Example, 100 grams of the formulation is made by using 20 grams each of Dried roots of *Salacia oblonga*, dried leaves or seeds or seeds kernels of *Mangifera indica*, Dried rhizomes of *Cyperus rotundus*, Dried fruits of *Terminalia chebula* and dried Fruits with seeds and stem bark of *Zizyphus jujuba*.

The herbs are taken in the above proportion and powdered. The powders are mixed to get the composition of the Example 1. The composition prepared as described above is dispensed as sachets containing 6 grams in it. The content of the sachet is to be added to one and half to two liters of water in a suitable vessel and boiled for two minutes. Then the powdered composition is to be strained and removed from the vessel to be dispensed off. The water so made is to be completely used up by the diabetic patient in twenty four hours, using it instead of drinking water, in 8 or 6 divided doses.

Example 14

As per this example; 100 grams of the formulation is made using 50 grams of Dried fruits of *Terminalia chebula*, 20 grams of Dried leaves or seeds or seeds kernels of *Mangifera indica* and 10 grams each Dried roots of *Salacia oblonga*, Fruits with seeds and stem bark of *Zizyphus jujuba* and Dried rhizomes of *Cyperus rotundus*.

The specified parts of the above mentioned herbs were taken in the above mentioned proportion and powdered. The powders were mixed to get the formulation. The formulation prepared as described above is dispensed as packet with single dose content of 12.5 grams sachets containing 6 grams in each sachet. When used the content of the sachet is to be added to one and half to two liters of water in a suitable vessel and boiled for two minutes. Then the powdered composition is to be strained and removed from the vessel to be dispensed off. The water so made is to be completely used up by the diabetic patient in twenty four hours, in 8 or 6 divided doses.

Example 15

In this Example 15 of the invention, 100 grams of the composition is made using 30 grams each of Dried fruits of *Terminalia chebula* and Dried roots of *Salacia oblonga*, 15 grams each of Dried rhizomes of *Cyperus rotundus* and Dried fruits of *Zizyphus jujube* and 10 grams of Dried seed kernels of *Mangifera indica*.

The herbs are taken in the above proportion mixed and made into coarse powder using a pulveriser. The powder so made is extracted using water as a solvent. Water from the resultant extract is completely evaporated to get dried flakes of the extract which is then again powdered to get fine powder of the composition which makes up the active ingredient part of the formulation of the invention described in this Example 15.

This active ingredient powder of the formulation constitutes 0.625 grams of the 1 gram tablets. The rest of the 0.375 grams of each of the 1 gram tablet is constituted by binders and exciepients of which some are digestive, flavoring and absorptive adjuvants. The composition of the exciepients and binders in a 1 gram tablet is 0.022 grams of *Ipomoea batatas*, 0.017 grams of *Elettaria cardamom*, 0.023 grams of *Piper longum*, 0.0145 grams of *Cuminum ciminum* 0.016 grams of Di-calcium Phosphate IP, 0.015 grams of PVPK-30, 0.0004 grams each of Methyl paraben IP, Propyl paraben IP and colloidal silicon dioxide-IP, 0.0003 grams of talcum powder, 0.001 gram of Magnesium Stearate, 0.06 grams of Microcrystalline cellulose powder, 0.2 grams of IPA-IP and 0.005 grams of Aspartame, together constituting 0.375 grams. Tablets are made using these ingredients in the above said ratio and in the conventional methods of tablet making.

The above embodiment of the formulation as a tablet is orally administered to the hypertensive patient as one tablet, four times a day. The tablet is to be sublingually placed to dissolve over ten minutes before food or to be chewed and swallowed by the patient within ten minutes after food.

Utility of the Invention

The main advantage of the invention, for the prevention and treatment of diabetes and associated complications is that it provides safe and effective herbal formulation which simultaneously reduces the blood glucose levels of a diabetic as well as offer prevention and treatment for possible associated complications of diabetes. The same formulation also:
1. reduces the blood glucose level and thereby offers better control over diabetes mellitus.
2. offers good glycaemic control and reduces the glycosylation of hemoglobin.
3. reduces the total cholesterol levels, LDL cholesterol levels, increases the HDL cholesterol levels, reduces VLDL cholesterol levels, the Serum Triglyceride levels and thereby offers better management of the lipid profile
4. improves the renal health and function, decreases the incidence of urinary tract infections, and reduces serum creatinine levels.

5. reduces the size of the prostrate gland significantly in diabetic patients suffering from benign prostatic hypertrophy.
6. reduces the pain and numbness associated with peripheral neuropathy usually affecting diabetic patients.
7. has significant medicinal values useful in improvement of insulin sensitivity, reduction of hyperglycemia, reduction in hypoglycemic drug dependency and improvement in the general health of diabetics.
8. is an equally good or significantly better option of prophylactic diabetic control for people with identified pre-diabetic conditions when compared with diet and exercise alone or as an adjuvant to diet and exercise.
9. is an equally good or significantly better option of diabetic control for newly identified diabetics when compared with diet and exercise alone or as an adjuvant to diet and exercise.
10. is an excellent adjuvant with other anti-diabetic drugs and reduces the need of other hypoglycemics.
11. improves the cardiovascular health, reduces hypertension, improves the ratio of the serum lipid profile and improves performance in exercise tolerance test of a diabetic cardiac patient.
12. prevents retinal damages, cataract and deterioration of vision usually associated with diabetes, thus ensuring a better quality of life for them.
13. augments wound healing of diabetic ulcers as evidenced by reduced time in complete healing of these ulcers.
14. can be made into diverse pharmaceutical preparations such as tablets, capsules, granules, herbal health drink, fermented herbal nutraceutical beverage, high-fiber nutraceutical food stuff(s), inhalable herbal medicinal preparation(s), ocular preparation(s), transdermal absorbable preparation(s) and the like.

Main advantage of the invention, for the prevention and treatment of diabetes is that it provides safe and effective herbal formulation which simultaneously reduces the blood glucose levels of a diabetic as well as offer prevention for prediabetic pateints. The same formulation also:
1. reduces the blood glucose level and thereby offers better control over diabetes mellitus.
2. offers good glycaemic control and reduces the glycosylation of hemoglobin.
3. offers an equally good or significantly better option for people with identified pre-diabetic conditions when compared with diet and exercise alone or as an adjuvant to diet and exercise and a process for the preparation of the same.
4. is an equally good or significantly better option of diabetic control for newly identified diabetics when compared with diet and exercise alone or as an adjuvant to diet and exercise.
5. is an excellent adjuvant with other anti-diabetic drugs and reduces the need of other hypoglycemics.
6. can be made into diverse pharmaceutical preparations such as tablets, capsules, granules, syrups, herbal health drink, fermented herbal nutraceutical beverage, high-fiber nutraceutical food stuff(s), inhalable herbal medicinal preparation(s), ocular preparation(s), transdermal absorbable preparation(s) and the like.

Another main advantage of the invention for the prevention and treatment of renal complications associated with diabetes is that it provides safe and effective herbal formulation for prevention and treatment of renal complications associated with diabetes which simultaneously reduces the reduce the elevated levels of serum creatinine. The same formulation also:
1. improves the renal cellular health and thereby reduces the elevated levels of serum creatinine.
2. improves the renal health and function, decreases the incidence of urinary tract infections, and reduces serum creatinine levels.
3. is an excellent adjuvant with other renal supportive drugs.
4. can be made into diverse pharmaceutical preparations such as tablets, capsules, granules, herbal health drink, fermented herbal nutraceutical beverage, high-fiber nutraceutical food stuff(s), inhalable herbal medicinal preparation(s), ocular preparation(s), transdermal absorbable preparation(s) and the like.

Another main advantage of the invention for the prevention and treatment of diabetic retinopathy is that it it provides safe and effective herbal formulation which prevents, manages and treats retinopathy associated with diabetes and offers arrest to the progress of the disease. The same formulation also:
a. arrests the progress of retinopathy associated with diabetes.
b. offers prevention of retinopathy associated with diabetes in diabetic patients.
c. is an excellent adjuvant with other anti-diabetic drugs.
d. prevents retinal damages, cataract and deterioration of vision usually associated with diabetes, thus ensuring a better quality of life for them.
e. can be made into diverse pharmaceutical preparations such as tablets, capsules, granules, herbal health drink, fermented herbal nutraceutical beverage, high-fiber nutraceutical food stuff(s), inhalable herbal medicinal preparation(s), ocular preparation(s), transdermal absorbable preparation(s) and the like.

Another main advantage of invention for preventing oxidative damage to heart and blood vessels is that it provides safe and effective herbal formulation which simultaneously prevents oxidative damage to heart and its blood vessels and also reduces hypertension. The same formulation also:
1. reduces systolic and diastolic blood pressure and thereby offers better control over hypertension.
2. offers good antioxidant support to cardiac muscles and blood vessels and prevents stress related oxidative damage to it.
3. has significant medicinal values useful reduction in hypertensive drug dependency and improvement in the general health of hypertensive patients.
4. is an equally good or significantly better option of prophylactic blood pressure control for people with identified pre-hypertensive conditions when compared with diet and exercise alone or as an adjuvant to diet and exercise.
5. is an equally good or significantly better option of blood pressure control for newly identified hypertensives when compared with diet and exercise alone or as an adjuvant to diet and exercise.
6. is an excellent adjuvant with other anti-hypertensive drugs and reduces the need of other anti-hypertensives, considerably.
7. can be made into diverse pharmaceutical preparations such as tablets, capsules, granules, herbal health drink, fermented herbal nutraceutical beverage, high-fiber nutraceutical food stuff(s), inhalable herbal medicinal preparation(s), ocular preparation(s), transdermal absorbable preparation(s) and the like.

The invention claimed is:

1. A herbal formulation for the treatment of diabetes and associated complications comprising the following ingredients:
   a) Fruits without seeds of the Species *Emblica officinalis* Gaertn. of the Euphorbiaceae Family, 5 to 8% by w/w;
   b) Roots of Species of herbs of the Genus *Salacia* of the Celastraceae family, 10 to 15% by w/w;
   c) Seeds of the Species *Strychnos potatorum* L. f. of the Strychnaceae family, 5 to 8% by w/w;
   d) Roots of the Species *Vetiveria zizanioides* (L.) Nash of the Poaceae family, 1 to 5% by w/w;
   e) Rhizomes of the Species *Curcuma longa* L. of the Zingiberaceae family, 5 to 8% by w/w;
   f) Whole plant of Species of herbs of the Genus *Aerva* of the Amaranthaceae family, 5 to 8% by w/w;
   g) Whole plant of Species of herbs of the Genus *Biophytum* of the Oxalidaceae family, 1 to 5% by w/w;
   h) Seeds of Species of herbs of the Genus *Syzygium* of the Myrtaceae family, 5 to 8% by w/w;
   i) Seeds kernels of the Species *Mangifera indica* L. of the Anacardiaceae family, 1 to 5% by w/w;
   j) Tuberous roots of Species of herbs of the Genus *Cyclea* and/or roots of the Genus *Cissampelos* of the Menispermaceae family, 1 to 5% by w/w;
   k) Seeds of Species of herbs of the Genus *Embelia* of the Myrsinaceae family, 1 to 5% by w/w;
   l) Rhizomes of Species of herbs of the Genus *Cyperus* of the Cyperaceae family, 1 to 5% by w/w;
   m) Fruits without seeds of the Species *Terminalia chebula* (Gaertn.) Retz. of the Combretaceae family, 15 to 30% by w/w;
   n) Whole plant of the Species *Centella asiatica* (L.) Urban of the Apiaceae family and/or leaves of the Species *Strychnos nux-vomica* L. of the Strychnaceae family, and/or flowers of the Species *Butea frondosa* Koen. ex Roxb. Taub. of the Papilionaceae family and/or heart wood of the Species *Acacia catechu* (L.f.) Willd. of the Mimosaceae family, 1 to 5% by w/w;
   o) Stem with bark of the Species *Coscinium fenestratum* (Gaertn.) Colebr. of the Menispermaceae family and/or stem with bark of Species of herbs of the Genus *Berberis* of the Berberidaceae family, 5 to 8% w/w; and
   p) Fruits with seeds and stem bark of Species of herbs of the Genus *Zizyphus* of the Rhamnaceae family, 1 to 5% by w/w,
   wherein the ingredients are powdered to 1 millimeter to 3 millimeter particle size and blended in a blender at 30 to 60 rotations per minutes to obtain the homogenous herbal formulation.

2. A herbal formulation according to claim 1 wherein the Species of the Genus *Salacia* of the Celastraceae family are *Salacia oblonga* Wall, ex Wight & Arn. and/or *Salacia reticulata* Wight and/or, *Salacia chinensis* L. and/or *Salacia fruticosa* Heyne, and/or *Salacia macrosperma* Wight.

3. A herbal formulation according to claim 1, wherein the Species of the Genus *Aerva* of the Amaranthaceaea family are *Aerva lanata* Juss., and/or *Aerva javanica* (Burm. f.) Juss. ex J. A. Schultes.

4. A herbal formulation according to claim 1, wherein the Species of the Genus *Biophytum* of the Oxalidaceae family are *Biophytum sensitivum* (L.) DC. and/or *Biophytum reinwardtii* Edgw. & Hk. f.

5. A herbal formulation according to claim 1, wherein the Species of the Genus *Syzygium* of the Myrtaceae family are *Syzygium cumini* (L.) Skeels and/or *Syzygium caryophyllaeum* Gaertn.

6. A herbal formulation according to claim 1, wherein the Species of the Genus *Cyclea* is *Cyclea peltata* (Lam.) Hook. f. & Thorns, and/or Species of the Genus *Cissampelos* is *Cissampelos pareira* L. of the Menispermaceae family.

7. A herbal formulation according to claim 1, wherein the Species of the Genus *Embelia* of the Myrsinaceae family are *Embelia ribes* Burm. f. and/or *Embelia tsjerium-cottam* A. DC.

8. A herbal formulation according to claim 1, wherein the Species of the Genus *Cyperus* of the Cyperaceae family are *Cyperus rotundus* L., and/or *Cyperus esculentus* L. and/or *Cyperus scariosus* R. Br.

9. A herbal formulation according to claim 1, wherein the Species of the Genus *Berberis* of the Berberidaceae family are *Berberis aristata* DC. var. aristata and/or *Berberis calliobotrys* Aitch. ex Koehne and/or *Berberis lycium* Royle and/or *Berberis orthobotrys* Bien. ex. Aitch. and/or *Berberis umbellata* Wall, ex G. Don. and/or *Berberis vulgaris* L. of the Berberidaceae family.

10. An herbal formulation according to claim 1, wherein the Species of the Genus *Zizyphus* of the Rhamnaceae family are *Zizyphus jujuba* Lamk., and/or *Zizyphus xylopyrus* (Retz.) Willd. and/or *Zizyphus jujuba* Mill. and/or *Zizyphus oenoplia* (L.) Mill, and/or *Zizyphus rugosa* Lamk., and/or *Zizyphus glabrata* Heyne ex Roth and/or *Zizyphus nummularia* (Burm. f.) Wt. & Arn.

11. An herbal formulation according to claim 1 formulated as synergistic herbal combination powder or processed as fermented herbal nutraceutical beverage or high-fiber nutraceutical food stuff(s) or extract/concentrate which is further formulated using known conventional processes to tablets, capsules, granules, syrups, herbal health drink, inhalable herbal medicinal preparations, ocular preparations, or transdermal absorbable preparations including ointments, gels, or injectable medicine.

12. The herbal formulation of claim 11, wherein the extract/concentrate is further formulated with suitable digestive, flavoring, binding, sweetening and excipient and/or absorptive adjuvants.

* * * * *